United States Patent
Talbot et al.

(10) Patent No.: US 7,727,148 B2
(45) Date of Patent: Jun. 1, 2010

(54) SENSING SYSTEM WITH AUXILIARY DISPLAY

(75) Inventors: Cary D. Talbot, Santa Clarita, CA (US);
John J. Mastrototaro, Los Angeles, CA (US); Rajiv Shah, Palos Verdes, CA (US); Edward Chernoff, Frazier Park, CA (US); John C. Mueller, Jr., Simi Valley, CA (US); Varaz Shahmirian, Northridge, CA (US); Richard E. Purvis, Pasadena, CA (US); Wayne A. Morgan, Northridge, CA (US); Rebecca K. Gottlieb, Culver City, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 0 days.

(21) Appl. No.: 11/980,149

(22) Filed: Oct. 30, 2007

(65) Prior Publication Data
US 2008/0064943 A1   Mar. 13, 2008

Related U.S. Application Data

(63) Continuation of application No. 10/899,623, filed on Jul. 27, 2004, now Pat. No. 7,344,500.

(51) Int. Cl.
*A61B 5/00* (2006.01)
(52) U.S. Cl. ............... 600/365; 600/345; 600/347
(58) Field of Classification Search .......... 600/316, 600/347, 365
See application file for complete search history.

(56) References Cited

U.S. PATENT DOCUMENTS

| 4,433,072 A | 2/1984 | Pusineri et al. |
| 4,494,950 A | 1/1985 | Fischell |
| 4,562,751 A | 1/1986 | Nason et al. |
| 4,671,288 A | 6/1987 | Gough |

(Continued)

FOREIGN PATENT DOCUMENTS

EP        1338295        8/2003

(Continued)

OTHER PUBLICATIONS

Reach et al., "Experience with an implantable glucose sensor as a prerequisite of an artificial beta cell," Biomed. Biochim. Acta, 1984, pp. 577-584, vol. 5.

(Continued)

*Primary Examiner*—Patricia C Mallari
*Assistant Examiner*—Karen E Toth
(74) *Attorney, Agent, or Firm*—Pillsbury Winthrop Shaw Pittman LLP

(57) ABSTRACT

A system is provided for sensing blood glucose data of a patient. The system includes a sensor, user interface, and an optional auxiliary device. If the connection between the sensor and user interface is by a wire, the sensor remains powered when the wire is disconnected. The communication between the sensor and the user interface may be wireless. The auxiliary device can be a patient monitor or other display or signal device, which displays information about the blood glucose data collected by the sensor. The sensor is connected to sensor electronics, which include a sensor power supply, a voltage regulator, and optionally a memory and processor.

6 Claims, 26 Drawing Sheets

U.S. PATENT DOCUMENTS

| | | | |
|---|---|---|---|
| 4,678,408 A | 7/1987 | Nason et al. | |
| 4,685,903 A | 8/1987 | Cable et al. | |
| 4,731,726 A | 3/1988 | Allen, III | |
| 4,781,798 A | 11/1988 | Gough | |
| 4,871,351 A | 10/1989 | Feingold | |
| 5,080,653 A | 1/1992 | Voss et al. | |
| 5,097,122 A | 3/1992 | Colman et al. | |
| 5,101,814 A | 4/1992 | Palti | |
| 5,108,819 A | 4/1992 | Heller et al. | |
| 5,165,407 A | 11/1992 | Wilson et al. | |
| 5,262,035 A | 11/1993 | Gregg et al. | |
| 5,262,305 A | 11/1993 | Heller et al. | |
| 5,264,104 A | 11/1993 | Gregg et al. | |
| 5,264,105 A | 11/1993 | Gregg et al. | |
| 5,284,140 A | 2/1994 | Allen et al. | |
| 5,299,571 A | 4/1994 | Mastrototaro | |
| 5,320,725 A | 6/1994 | Gregg et al. | |
| 5,322,063 A | 6/1994 | Allen et al. | |
| 5,356,786 A | 10/1994 | Heller et al. | |
| 5,370,622 A | 12/1994 | Livingston et al. | |
| 5,371,687 A | 12/1994 | Holmes, II et al. | |
| 5,376,070 A | 12/1994 | Purvis et al. | |
| 5,390,671 A | 2/1995 | Lord et al. | |
| 5,391,250 A | 2/1995 | Cheney, II et al. | |
| 5,403,700 A | 4/1995 | Heller et al. | |
| 5,411,647 A | 5/1995 | Johnson et al. | |
| 5,482,473 A | 1/1996 | Lord et al. | |
| 5,497,772 A * | 3/1996 | Schulman et al. | 600/347 |
| 5,543,326 A | 8/1996 | Heller et al. | |
| 5,569,186 A | 10/1996 | Lord et al. | |
| 5,586,553 A | 12/1996 | Halili et al. | |
| 5,593,852 A | 1/1997 | Heller et al. | |
| 5,660,163 A | 8/1997 | Schulman et al. | |
| 5,665,065 A | 9/1997 | Colman et al. | |
| 5,665,222 A | 9/1997 | Heller et al. | |
| 5,750,926 A | 5/1998 | Schulman et al. | |
| 5,779,665 A | 7/1998 | Mastrototaro et al. | |
| 5,791,344 A | 8/1998 | Schulman et al. | |
| 5,904,708 A | 5/1999 | Goedeke | |
| 5,917,346 A | 6/1999 | Gord et al. | |
| 5,961,451 A * | 10/1999 | Reber et al. | 600/322 |
| 5,965,380 A | 10/1999 | Heller et al. | |
| 5,972,199 A | 10/1999 | Heller et al. | |
| 5,978,236 A | 11/1999 | Faberman et al. | |
| 5,999,848 A | 12/1999 | Gord et al. | |
| 5,999,849 A | 12/1999 | Gord et al. | |
| 6,043,437 A | 3/2000 | Schulman et al. | |
| 6,081,736 A | 6/2000 | Colvin et al. | |
| 6,083,710 A | 7/2000 | Heller et al. | |
| 6,088,608 A | 7/2000 | Schulman et al. | |
| 6,103,033 A | 8/2000 | Say et al. | |
| 6,119,028 A | 9/2000 | Schulman et al. | |
| 6,120,676 A | 9/2000 | Heller et al. | |
| 6,121,009 A | 9/2000 | Heller et al. | |
| 6,134,461 A | 10/2000 | Say et al. | |
| 6,143,164 A | 11/2000 | Heller et al. | |
| 6,162,611 A | 12/2000 | Heller et al. | |
| 6,175,752 B1 * | 1/2001 | Say et al. | 600/345 |
| 6,248,067 B1 * | 6/2001 | Causey et al. | 600/365 |
| 6,259,937 B1 | 7/2001 | Schulman et al. | |
| 6,329,161 B1 | 12/2001 | Heller et al. | |
| 6,424,847 B1 | 7/2002 | Mastrototaro et al. | |
| 6,472,122 B1 | 10/2002 | Schulman et al. | |
| 6,484,046 B1 | 11/2002 | Say et al. | |
| 6,503,381 B1 | 1/2003 | Gotoh et al. | |
| 6,514,718 B2 | 2/2003 | Heller et al. | |
| 6,553,263 B1 | 4/2003 | Meadows et al. | |
| 6,554,798 B1 | 4/2003 | Mann et al. | |
| 6,558,320 B1 | 5/2003 | Causey, III et al. | |
| 6,560,741 B1 | 5/2003 | Gerety et al. | |
| 6,561,978 B1 * | 5/2003 | Conn et al. | 600/309 |
| 6,565,509 B1 | 5/2003 | Say et al. | |
| 6,579,690 B1 | 6/2003 | Bonnecaze et al. | |
| 6,591,125 B1 | 7/2003 | Buse et al. | |
| 6,592,745 B1 | 7/2003 | Feldman et al. | |
| 6,605,200 B1 | 8/2003 | Mao et al. | |
| 6,605,201 B1 | 8/2003 | Mao et al. | |
| 6,607,658 B1 | 8/2003 | Heller et al. | |
| 6,616,819 B1 | 9/2003 | Liamos et al. | |
| 6,618,934 B1 | 9/2003 | Feldman et al. | |
| 6,623,501 B2 | 9/2003 | Heller et al. | |
| 6,654,625 B1 | 11/2003 | Say et al. | |
| 6,671,554 B2 | 12/2003 | Gibson et al. | |
| 6,676,816 B2 | 1/2004 | Mao et al. | |
| 6,689,265 B2 | 2/2004 | Heller et al. | |
| 6,733,471 B1 | 5/2004 | Ericson et al. | |
| 6,743,635 B2 * | 6/2004 | Neel et al. | 436/95 |
| 6,746,582 B2 | 6/2004 | Heller et al. | |
| 6,749,740 B2 | 6/2004 | Liamos et al. | |
| 6,809,653 B1 | 10/2004 | Mann et al. | |
| 6,881,551 B2 | 4/2005 | Heller et al. | |
| 6,893,545 B2 | 5/2005 | Gotoh et al. | |
| 6,916,159 B2 | 7/2005 | Rush et al. | |
| 6,931,327 B2 | 8/2005 | Goode, Jr. et al. | |
| 6,932,894 B2 | 8/2005 | Mao et al. | |
| 6,942,518 B2 | 9/2005 | Liamos et al. | |
| 2002/0068858 A1 | 6/2002 | Braig et al. | |
| 2002/0082665 A1 | 6/2002 | Haller et al. | |
| 2002/0137997 A1 | 9/2002 | Mastrototaro et al. | |
| 2002/0161288 A1 | 10/2002 | Shin et al. | |
| 2003/0023171 A1 | 1/2003 | Sato et al. | |
| 2003/0050541 A1 | 3/2003 | Wuori | |
| 2003/0078560 A1 | 4/2003 | Miller et al. | |
| 2003/0088166 A1 | 5/2003 | Say et al. | |
| 2003/0100821 A1 | 5/2003 | Heller et al. | |
| 2003/0144581 A1 | 7/2003 | Conn et al. | |
| 2003/0152823 A1 | 8/2003 | Heller et al. | |
| 2003/0168338 A1 | 9/2003 | Gao et al. | |
| 2003/0176183 A1 | 9/2003 | Drucker et al. | |
| 2003/0188427 A1 | 10/2003 | Say et al. | |
| 2003/0199744 A1 | 10/2003 | Buse et al. | |
| 2003/0220552 A1 | 11/2003 | Reghabi et al. | |
| 2004/0061232 A1 | 4/2004 | Shah et al. | |
| 2004/0061234 A1 | 4/2004 | Shah et al. | |
| 2004/0064133 A1 | 4/2004 | Miller et al. | |
| 2004/0064156 A1 | 4/2004 | Shah et al. | |
| 2004/0074785 A1 | 4/2004 | Holker et al. | |
| 2004/0093167 A1 | 5/2004 | Braig et al. | |
| 2004/0111017 A1 | 6/2004 | Say et al. | |
| 2005/0038331 A1 | 2/2005 | Silaski et al. | |
| 2005/0192557 A1* | 9/2005 | Brauker et al. | 604/503 |
| 2005/0214585 A1 | 9/2005 | Li et al. | |
| 2006/0052745 A1 | 3/2006 | Van Antwerp et al. | |
| 2006/0229694 A1 | 10/2006 | Schulman et al. | |

FOREIGN PATENT DOCUMENTS

| | | |
|---|---|---|
| WO | WO 96/37246 A1 | 11/1996 |
| WO | WO 00/19887 A1 | 4/2000 |
| WO | WO 02/058537 A2 | 8/2002 |

OTHER PUBLICATIONS

Abel et al., "A Method for Evaluating in vivo the Functional Characteristics of Glucose Sensors," Biosensors, 1986, pp. 211-220, vol. 2.

Boguslavsky et al., "Applications of redox polymers in biosensors," Solid State Ionics, 1993, pp. 189-197, vol. 60.

Geise et al., "Electropolymerized 1,3-diaminobenzene for the construction of a 1-1'-dimethylferrocene mediated glucose biosensor,"Analytica Chim. Acta.,1993, pp. 467-473, v18.

Gernet et al., "A planar glucose enzyme electrode," Sensors and Actuators, 1989, pp. 537-540, vol. 17, Elsevier Sequoia, Netherlands.

Gernet et al., "Fabrication and Characterization of a Planar Electrochemical Cell and Its Applications as a Glucose Sensor," Sensors and Actuators, 1989, pp. 49-70, vol. 18.

Gorton et al., "Amperometric glucose senosrs based on immobilized glucose-oxidizing enzymes and chemically modified electrodes," Analytica Chim Acta., 1991, pp. 43-54, v. 249.

Gorton et al., "Amperometric biosensors based on an apparent direct electron transfer between electrodes and immobilized peroxidases," Analyst, 1992, pp. 1235-1241, vol. 117.

Gough et al., "Two-Dimensional Enzyme Electrode Sensor for Glucose," Analytical Chemistry, 1985, pp. 2351-2357, vol. 57.

Gregg et al., "Redox polymer films containing enzymes," J. Phys. Chem., 1991, pp. 5970-5975.

Gregg et al., "Cross-Linked Redox Gels Containing Glucose Oxidase for Amperometric Biosensor Applications," Anal. Chem., 1990, pp. 258-263, vol. 62.

Heller et al., "Electrical Wiring of Redox Enzymes," Accounts of Chemical Research, 1990, pp. 128-134, vol. 23, No. 5.

Johnson et al., "In vivo evaluation of an electroenzymatic glucose sensor implanted in subcutaneous tissue," Biosensors & Bioelectronics, 1992, pp. 709-714, vol. 7.

Jonsson et al., "An Electrochemical Sensor for Hydrogen Peroxide Based on Peroxidase Adsorbed on a Spectrographic Graphite Electrode," Electroanalysts, 1989, pp. 465-468, v.1.

Kanapieniene et al., "Miniature glucose biosensor with extended linearity," Sensors and Actuators, 1992, pp. 37-40, vol. B, No. 10.

Kawamori et al., "Perfect Normalization of Excessive Glucagon Responses to Intravenous Arginine in Human Diabetes Mellitus With . . . ," Diabetes, 1980, pp. 762-765, vol. 29.

Kimura et al., "An immobilized Enzyme Membrane Fabrication Method using an Ink Jet Nozzle," Biosensors, 1988, pp. 41-52, vol. 4.

Koudelka et al., "In-vivio Behaviour of Hypodermically Implanted Microfabricated Glucose Sensors," Biosensors & Bioelectronics, 1991, pp. 31-36, vol. 6.

Mastrototaro et al., "An electroenzymatic glucose sensor fabricated on a flexible substrate," Sensors and Actuators, 1991, pp. 139-144, vol. 5.

Mastrototaro et al., "An Electroenzymatic Sensor Capable of 72 Hour Continuous Monitoring of Subcutaneous Glucose," 14th Int'l Diabetes Federation Congress, 1991.

McKean et al., "A Telemetry-Instrumentation System for Chronically Implanted Glucose and Oxygen Sensors," IEEE Transactions on Biomedical Eng., 1988, pp. 526-532, vol. 35, No. 7.

Monroe, "Novel implantable glucose sensors," ACL, 1989, pp. 8-16.

Morff et al., "Microfabrication of Reproducible, Economical, Electroenzymatic Glucose Sensors," Annual Int'l Conf. IEEE Eng. in Med. and Bio. Soc., 1990, pp. 483-484, v.12, n.2.

Nakamado et al., "A Lift-Off Method for Patterning Enzyme-Immobilized Membranes in Multi-Biosensors," Sensors and Actuators, 1988, pp. 165-172, vol. 13.

Nishida et al., "Clinical applications of the wearable artificial endocrine pancreas with the newly designed . . . ," Path. and Treat. of NIDDM . . . , 1994, p. 353-358, No. 1057.

Shichiri et al., "An artificial endocrine pancrease—problems awaiting solutions for long term clinical applications of . . . ," Frontiers Med. Biol. Eng., 1991, pp. 283-292, v.3.

Shichiri et al., "Wearable Artificial Endocrine Pancreas with Needle-Type Glucose Sensor," The Lancet, 1982, pp. 1129-1131, vol. 2 (8308).

Shichiri et al., "Telemetry Glucose Monitoring Device with Needle-Type Glucose Sensor," Diabetes Care, May-Jun. 1986, pp. 298-301, vol. 9, No. 3.

Shichiri et al., "Normalization of the Paradoxic Secretion of Glucagen in Diabetics Who Were Controlled by the Artificial Beta Cell," Diabetes, 1979, pp. 272-275, vol. 28.

Shichiri et al., "Closed-Loop Glycemic Control with a Wearable Artificial Endocrine Pancreas," Diabetes, 1984, pp. 1200-1202, vol. 33.

Shichiri et al., "In Vivo Characteristics of Needle-Type Glucose Sensor," Hormone and Metabolic Research, 1988, pp. 17-20, vol. 20.

Shichiri et al., "A Needle-Type Glucose Sensor," Life Support Systems: The Journal of the European Society for Artificial Organs, 1984, pp. 7-9, vol. 2, supplement 1.

Shichiri et al., "The Wearable Artificial Endocrine Pancreas with a Needle-Type Glucose Sensor," Acta Pediatr, Jpn, 1984, pp. 358-370, vol. 26.

Shichiri et al., "Glycaemic Control in Pancreatectomized Dogs with a Wearable Artificial Endocrine Pancreas," Diabetologica, 1983, pp. 179-184, vol. 24.

Shichiri et al., "Membrane design for extending the long-life of an implantable glucose sensor," Diab. Nutr. Metab., 1989, pp. 309-313, vol. 2.

Shinkai et al., "Molecular Recognition of Mono- and Di-Saccharides by Phenylboronic Acids in Solvent Extraction and as a Monolayer," J. Chem. Soc., 1991, pp. 1039-1041.

Tamiya et al., "Micro Glucose Sensors Usind Electron Mediators Immobilized on a Polypyrrole-Modified Electrode," Sensors and Actuators, 1989, pp. 297-307, v.18.

Tsukagoshi et al., "Specific Complexation with Mono- and Disaccharides That Can Be Detected by Circular Dichroism," J. Org. Chem., 1991, pp. 4089-4091, vol. 56.

Urban et al., "Minaturized multi-enzyme biosensors integrated with pH sensors on flexible polymer carriers . . . ," Biosensors & Bioelectronics, 1992, pp. 733-739, vol. 7.

Urban et al., "Miniaturized thin-film biosensors using covalently immobilized glucose oxidase," Biosensors & Bioelectronics, 1991, pp. 555-562, vol. 6.

Velho et al., "In vivo calibration of a subcutaneous glucose sensor for determination of subcutaneous glucose kinetics," Diab. Nutr. Metab., 1988 pp. 227-233, v.3.

Yokoyama et al., "Integrated Biosensor for Glucose and Galactose," Analytica Chimica Acta., 1989, pp. 137-142, vol. 218.

Nishida et al., "Development of a ferrocene-mediated needle-type glucose sensor . . . ," Medical Process Through Technology, 1995, pp. 91-103, vol. 21.

Koudelka et al., "Planar Amperometric Enzyme-Based Glucose Microelectrode," Sensors and Actuators, 1989, pp. 157-165, vol. 18.

Yamasaki et al., "Direct measurement of whole blood glucose by a needle-type sensor," Clinica Chimica Acta., 1989, pp. 93-98, vol. 93.

Sternberg et al., "Study and Development of Multilayer Needle-type Enzyme-based Glucose Microsensors," Biosensors, 1988, pp. 27-40, vol. 4.

Shaw et al., "In vitro testing of a simply constructed, highly stable glucose sensor suitable for implantation . . . ," Biosensors & Bioelectronics, 1991, pp. 401-406, vol. 6.

Poitout et al., "A glucose monitoring system for on line estimation in man of blood glucose concentration using a miniaturized . . . ," Diabetologia, 1993, pp. 658-663, vol. 36.

Hashigushi et al., "Development of a Miniaturized Glucose Monitoring System by Combining a Needle-Type Glucose Sensor . . . ," Diabetes Care, 1994, pp. 387-389, v.17, n.5.

Jobst et al., "Thin-Film Microbiosensors for Glucose-Lactate Monitoring," Anal. Chem., 1996, p. 3173-79, vol. 68.

Shults et al., "A Telemetry-Instrumentation System for Monitoring Multiple Subcutaneously Implanted Glucose Sensors," IEEE Trans. on Biomed. Eng., 1994, pp. 937-942, v41, n. 10.

Wang et al., "Needle-Type Dual Microsensor for the Simultaneous Monitoring of Glucose and Insulin," Anal. Chem., 2001, pp. 844-847, vol. 73.

Moussey et al., "Performance of Subcutaneously Implanted Needle-Type Glucose Sensors Employing a Novel Trilayer Coating," Anal. Chem., 1993, 2072-77, vol. 65.

Bindra et al., "Design and In Vitro Studies of a Needle-Type Glucose Sensor for Subcutaneous Monitoring," Anal. Chem., 1991, pp. 1692-1696, vol. 63.

PCT International Search Report, dated Feb. 23, 2006 (6 pgs.).

* cited by examiner

SENSING SYSTEM WITH AUXILIARY DISPLAY

RELATED APPLICATION DATA

This is a continuation of U.S. patent application Ser. No. 10/899,623, filed Jul. 27, 2004, now U.S. Pat. No. 7,344,500.

BACKGROUND OF THE INVENTION

1. Field of the Invention

This invention relates generally to a sensing system including a physiological characteristic sensor, a user interface, and an auxiliary device. The invention more specifically relates to a blood glucose sensor which remains powered and performs functions when disconnected from communication with the user interface. The auxiliary device may be a display device.

2. Description of Related Art

Test strip meters are used to measure the blood glucose level for patients that do not have metabolic control. Frequent measurements are needed to intervene and control glucose levels, but frequently using a test strip meter is labor intensive. For example, in hospitals today, nurses need to take discrete blood glucose measurements from many patients each hour. An automated frequent measurement apparatus and process are needed to relieve nursing labor.

Medical sensing systems designed to measure a physiological characteristic of a patient generally consist of a sensor and a user interface for setting up the sensor and observing data from the sensor. Typically, the sensor requires power, which is supplied by the user interface or by electronics that accompany the sensor on the user's body. In some environments, it is inconvenient for a person to wear the sensor and the accompanying electronics or user interface, especially if the electronics are large such as a wall mounted display. For example, in a hospital, it is common to have patient monitors that display data about patients, such as heart rate, blood pressure and the like. If a sensor is in communication with a patient monitor, it may be needed or desired to remove the sensor. Yet, the patient cannot always remove the sensor as needed or desired, especially if the sensor is difficult to remove or if the sensor is a single use device, which must be replaced with a new sensor each time it is removed. Thus, new systems are needed that allow the patient to wear the sensor continuously, without the constant inconvenience of a user interface.

BRIEF SUMMARY OF THE INVENTION

In embodiments of the present invention, a sensing system is provided to measure a physiological characteristic of a patient. The physiological characteristic is preferably blood glucose concentration, but may also be, in addition or in lieu of blood glucose concentration, the concentration of oxygen, potassium, hydrogen potential (pH), lactate, one or more minerals, analytes, chemicals, proteins, molecules, vitamins, and the like, and/or other physical characteristics such as temperature, pulse rate, respiratory rate, pressure, and the like.

The sensing system includes a sensor and a user interface. The sensing system may also include an auxiliary device. The sensor may be a subcutaneous sensor, vascular sensor, or non-invasive sensor. The user interface may be a handheld device, such as a handheld computer, personal data assistant (PDA), telephone, remote control, and the like. The auxiliary device is preferably a patient monitor.

The sensor may be a blood glucose sensor, wired to a user interface, which is wired to an auxiliary device, preferably a patient monitor. The sensor may preferably be a real-time sensor. The user interface may provide power to the sensor and/or the monitor may provide power to the sensor. Alternatively, the monitor may recharge the user interface, which powers the sensor. The user interface may be detached from the patient monitor while the sensor is still powered and working. The user interface may transmit data wirelessly to the monitor. Alternatively, the glucose sensor may be wired to both a user interface and a patient monitor. The sensor may be powered by the user interface, monitor, or both.

A blood glucose sensor and sensor electronics may be wired to a user interface. The sensor and sensor electronics can detach from the user interface. The sensor may remain powered by the sensor electronics when they are detached from the user interface. The sensor electronics may also be recharged when attached to the user interface. The sensor and sensor electronics may retain power, reference values (e.g., for calibration), and sensor measurements when detached from a first user interface. The sensor and sensor electronics can then be attached to a second user interface where they will download sensor measurements to be displayed, and the sensor and sensor electronics will not require recalibration or warm up due to attaching with a second user interface.

A user interface or monitor may supply power to sensor electronics using a transformer, thus providing ground isolation between the user interface and the sensor electronics. The sensor electronics may include a connector for wired connection to a user interface or monitor. The user interface may include a wired connection for connecting to a patient monitor.

The sensor may include a connector for connecting to sensor electronics. The sensor electronics power supply may be activated when the sensor is connected.

Further according to the present invention, a blood glucose sensor and sensor electronics may communicate with a user interface, which communicates with a monitor. The communications may be wired or wireless. The blood glucose sensor and sensor electronics may communicate to both a user interface and a monitor.

The sensor electronics may include factory supplied reference values for a sensor. The factory supplied reference values may be stored in a nonvolatile memory, which can also be placed into a user interface for calibrating sensor signals. Reference values can be communicated to the sensor electronics or user interface directly from a blood glucose meter. The reference values can be downloaded to a personal computer or manually entered into a personal computer and then uploaded to the user interface and optionally sent to the sensor electronics. The reference values can be manually entered into the user interface and optionally sent to the sensor electronics.

The sensor electronics may include one or more of a sensor power supply, a regulator, a signal processor, a measurement processor, a measurement memory and a reference memory. The user interface may include one or more of a user interface power supply, a user interface processor, a reference memory, a measurement processor, a measurement memory, a signal processor, a regulator, and a mechanism for receiving data from an input device and/or sending data to an output device. The user interface and sensor electronics may either or both include a wireless communication mechanism.

BRIEF DESCRIPTION OF THE DRAWINGS

A detailed description of embodiments of the invention will be made with reference to the accompanying drawings, wherein like numerals designate corresponding parts in the figures.

DETAILED DESCRIPTION OF THE INVENTION

Figure 1A:
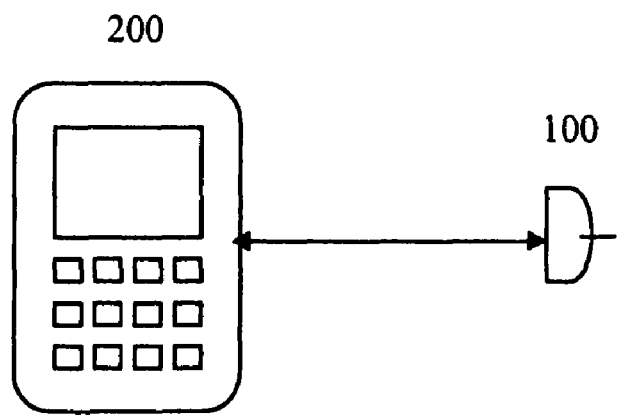
FIG. 1A is a communication flow diagram of a sensor and user interface in accordance with an embodiment of the present invention.

In the following description, reference is made to the accompanying drawings, which form a part hereof and which illustrate several embodiments of the present inventions. It is understood that other embodiments may be utilized and structural and operational changes may be made without departing from the scope of the present inventions.

As shown in the drawings for purposes of illustration, the invention may be embodied in a physiological characteristic sensing system including a physiological characteristic sensor, such as a blood glucose sensor, that generates physiological characteristic data to be sent to one or more devices, such as a user interface and/or an auxiliary device. The physiological) characteristic data may be displayed on the auxiliary device.

Physiological characteristics are generally used in a hospital to detect when a patient needs a therapy change and to quantify the therapeutic change required. For example, a patient's blood glucose level may be measured to determine if they have lost metabolic control. If they have lost metabolic control, a caregiver can use the blood glucose measurement to determine changes to therapy. Hospital patients may lack metabolic control due to trauma, stress of surgery, stroke, heart conditions, myocardial infarction, hypertension, diabetes, organ transplant, infections, sepsis, renal diseases, pregnancy, physical, mental or emotional distress, and the like.

In other embodiments, lactate sensors may be used to detect a patient's blood lactate concentration. Lactate concentrations can be used to detect whether a patient has had a myocardial infarction or whether a patient is septic. Rising lactate levels can indicate that a patient is becoming more septic, and lowering lactate levels can indicate that a patient is recovering from sepsis. Lactate levels may also be used to determine how efficiently a patient's tissue is using oxygen. As the tissue oxygen exchange decreases, the lactate level increases, and caregivers can detect that the patient is becoming more ill.

FIGS. 1A-1H show wired connections between a sensor 100 and one or more devices according to embodiments of the present invention. The one or more devices include at least a user interface 200 and may include one or more auxiliary devices 300. There may be a connector between wired components (not shown). As shown in FIG. 1A, the present invention may consist of a sensor 100 in communication with a user interface 200. The sensor 100 is powered by the user interface 200, and the sensor 100 measures a physiological characteristic, such as blood glucose concentration.

The sensor may continuously measure a physiological characteristic, and then measurement updates would be displayed periodically on one or more devices. The sensor measurements may be real-time, and thus would be displayed as soon as the measurement is available. Alternatively, more than one measurement may be collected before a measurement is displayed. The measurements also may be stored until all measurements are taken and then displayed. The measurement may also be delayed before it is displayed.

The sensor may also measure, in addition or in lieu of blood glucose concentration, the concentration of, oxygen, potassium, hydrogen potential (pH), lactate, one or more minerals, analytes, chemicals, proteins, molecules, vitamins, and the like, and/or other physical characteristics such as temperature, pulse rate, respiratory rate, pressure, and the like. The sensor may be an electrochemical sensor placed through skin into the subcutaneous tissue of a body such as the sensor described in U.S. Pat. Nos. 5,390,671, 5,391,250, 5,482,473, and 5,586,553, and U.S. patent application Ser. No. 10/273,767 (published as U.S. patent publication no. 2004/0074785 A1, Apr. 22, 2004), which are herein incorporated by reference. Alternatively, the sensor may be a blood contacting sensor. For example, the sensor may be a thin film vascular sensor such as described in U.S. Pat. Nos. 5,497,772, 5,660,163, 5,750,926, 5,791,344, 5,917,346, 5,999,848, 5,999,849, 6,043,437, 6,081,736, 6,088,608, 6,119,028, 6,259,937, 6,472,122, and 6,671,554, and U.S. patent application Ser. Nos. 10/034,627 (published as U.S. patent publication no. 2003/0078560 A1, Apr. 24, 2003), U.S. Ser. No. 10/331,186 (published as U.S. patent publication no. 2004/0061232 A1, Apr. 1, 2004), U.S. Ser. No. 10/671,996 (published as U.S. patent publication no. 2004/0061234 A1, Apr. 1, 2004), U.S. Ser. No. 10/335,574 (published as U.S. patent publication no. 2004/0064156 A1, Apr. 1, 2004), U.S. Ser. No. 10/334,686 (published as U.S. patent publication no. 2004/0064133 A1, Apr. 1, 2004), and U.S. Ser. No. 10/365,279 (published as U.S. patent publication no. 2003/0220552 A1, Nov. 27, 2003), which are herein incorporated by reference. Alternatively, the sensor may be non-invasive and thus, does not penetrate into the body such as optical sensors and the sensor described in U.S. patent application Ser. No. 09/465,715, (published as PCT application no. US99/21703, Apr. 13, 2000), which is herein incorporated by reference. The sensor may preferably be a real-time sensor. As used herein, the terms "real-time" and "real-time sensor" refer to a sensor that senses values substantially continuously over an extended period of time and makes such values available for use as the values are being sensed and collected rather than having to download substantially all the collected values at a later time for use. For example, a real-time blood glucose sensor might sense glucose values every 10 seconds over an extended period of 24 hours, and make the values available (e.g., processing, charting and displaying) every 5 minutes so that that users of an insulin pump have the flexibility to fine-tune and start or stop insulin delivery upon demand. Patients may thus use their pumps to make substantially immediate therapy adjustments based upon real-time continuous glucose readings displayed every 5 minutes and by viewing a graph with 24-hour glucose trends. For example, the sensor may be as described in U.S. patent application Ser. No. 10/141,375 (published as U.S. patent publication no. 2002/0161288 A1, Oct. 31, 2002), hereby incorporated by reference, and the view of displayed data may be as described in U.S. patent application Ser. No. 10/806,114, which is herein incorporated by reference.

In preferred embodiments, sensor measurements are displayed every 5 minutes. Alternatively they may be displayed more frequently such as every 2 minutes, every minute, or every 30 seconds. In other embodiments the sensor value is displayed less frequently such as every 7 minutes, 8 minutes, 10 minutes, 15 minutes, 20 minutes, 30 minutes, 1 hour, and the like. Periodically a nurse may observe a patient's present blood glucose level and adjust the patient's therapy such as changing the insulin delivery rate (e.g., increasing or decreasing the rate that a pump supplies insulin to the patient's body through intravenous or subcutaneous delivery), providing an extra bolus of insulin (e.g., injecting extra insulin into the patient's body, or into the patient's IV line, or by programming an insulin pump to infuse an extra dose of insulin), change the patient's food intake (e.g., increasing or decreasing the rate that glucose is delivered into the patient's body, or changing the rate of tube feeding, or giving the patient food to consume), changing the amount of drugs that the patient is using that affect insulin activity such as medications to treat type 2 diabetes, steroids, anti-rejection drugs, antibiotics, and the like. The nurse might check the patient's glucose level and make an adjustment to therapy as needed every hour. Alternatively, a nurse may see if an adjustment is needed more frequently such as every 30 minutes, 20 minutes, 10 minutes and the like. This is especially likely if the patient's glucose level is not in a normal range. Alternatively a nurse may see if an adjustment is needed less frequently such as every 2 hours, 3 hours, 4 hours, 6 hours and the like. This is more likely if the patient's glucose level is in the normal range; or, if the patient's glucose has been normal for a period such as 1 hour, 2 hours, 4 hours, or 8 hours; or if the patient's therapy has not changed for a period such as 2 hours, 4 hours, 8 hours or 12 hours. In further alternatives, nurses may rely on alarms to notify them to check on the patient. For example, nurses might rely on glucose alarms to tell them that glucose levels are too high or too low before they see if a therapy adjustment is needed, they might rely on an alarm to tell them that it is time to calibrate the sensor, they might rely on a time activated alarm to tell them that it is time to check in on a patient, they might rely on an alarm to tell them that the equipment needs to be cared for, and the like.

A normal range for a patient's blood glucose level in the hospital is typically between 80 and 120 milligrams of glucose per deciliter of blood (mg/dl). Some caregivers maintain a higher normal range with the upper limit of the range at about 140 mg/dl, 145 mg/dl, 150 mg/dl, 160 mg/dl, and the like and the lower limit of the range at about 70 ng/dl, 80 mg/dl, 90 mg/dl, 100 mg/dl, 110 mg/dl, and the like. Other caregivers maintain a lower normal range with the upper limit of the range at about 110 mg/dl, 100 mg/dl, 90 mg/dl, 80 mg/dl, and the like and the lower limit of the range at about 80 mg/dl, 70 mg/dl, 60 mg/dl, 50 mg/dl, and the like.

A caregiver may use the present blood glucose value to adjust a patient's therapy to bring the patient's glucose to within a normal range. For example, if the patient's glucose level is higher than the higher end of the normal range, the caregiver may increase the rate that insulin is delivered to the patient's body. Conversely, if the patient's glucose level is below the lower end of the normal range, the caregiver may decrease the insulin delivery rate.

Alternatively, the caregiver may consider both the present and at least one older glucose value to determine adjustments to the patient's therapy. For example, if the present glucose level is too high and a previous glucose level was lower, then the caregiver may substantially increase the insulin rate because the patient's glucose is too high and rising.

The caregiver may use trend information or a graphical plot of glucose values over time to determine if the patient's therapy should be changed. Alternatively, the therapy may be changed automatically when the patient's glucose level is drifting out of the normal range.

Figure 1B:
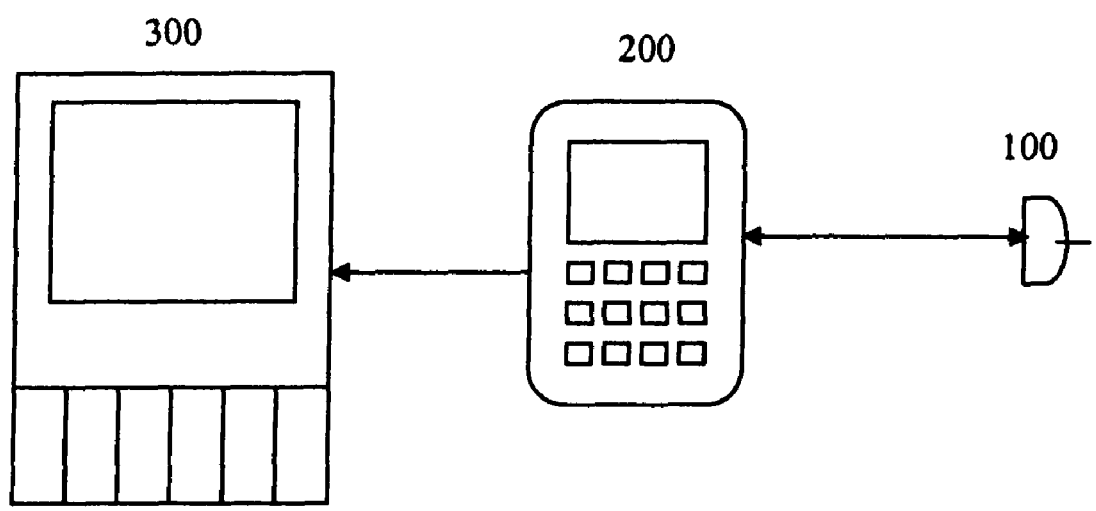
FIG. 1B is a communication flow diagram of a sensor and user interface and auxiliary device in accordance with an embodiment of the present invention.

The user interface 200 allows a user to interact with the sensor. The user interface may include one or more of: an output device such as a liquid crystal display (LCD), a light emitting diode (LED), a touch screen, a dot matrix display, plasma display, alarm, buzzer, speaker, sound maker, voice synthesizer, vibrator, and the like; an input device such as a keypad, one or more buttons, a keyboard, a mouse, a joystick, a radio frequency (RF) receiver, an infrared (IR) receiver, an optical receiver, a microphone, and the like. The user interface may be a handheld device such as a handheld computer, a personal digital assistant (PDA), a cell phone or other wireless phone, a remote control, and the like. Alternatively, the user interface may be a personal computer (PC), a desk top computer, a lap top computer, and the like, As shown in FIG. 1B, the user interface 200 may also be in communication with an auxiliary device 300, such as a patient monitor. A patient monitor includes any display or other indicator system intended to be used in a hospital, doctor's office, or other medical setting, including home medical use. For example, some patient monitors are used in a hospital environment to monitor physiological characteristics of a patient, such as the patient monitors described in U.S. Pat. No. 6,733,471, hereby incorporated by reference.

Although the arrow from the user interface 200 is shown transmitting data to auxiliary device 300 and not in reverse, this is not in any way intended to be limiting. In any of the figures shown, the transmission of data may occur in either, or both, directions. The communication may be over a wired connection or by wireless methods. Wireless methods include methods such as radio frequency (RF) communication, infrared (IR) communication, optical communication or any other wireless method that would be useful in connection with the present invention as would be readily appreciated by one of ordinary skill in the art without undue experimentation.

Figure 1C:
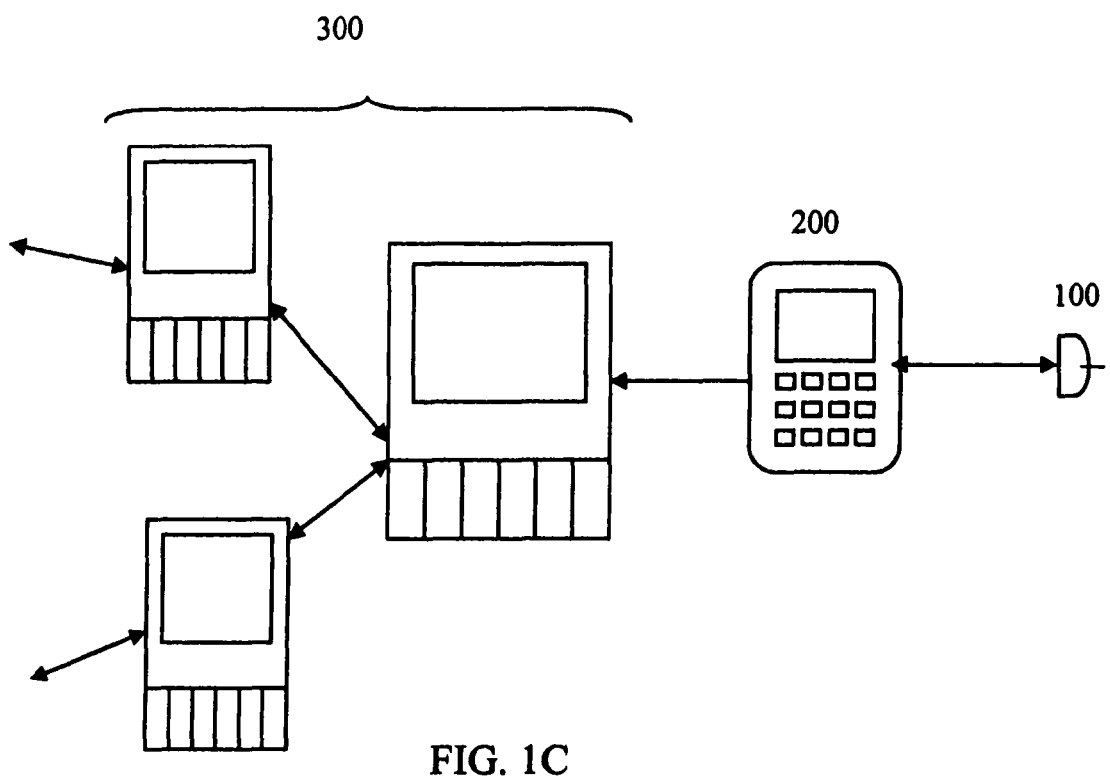
FIG. 1C is a communication flow diagram of a sensor and user interface and auxiliary devices in accordance with an embodiment of the present invention.

As shown in FIG. 1C, the user interface 200 may communicate with one or more auxiliary devices 300. The one or more auxiliary devices 300 may communicate with each other in addition to the user interface 200 and/or the sensor 100 directly.

Figure 1D:
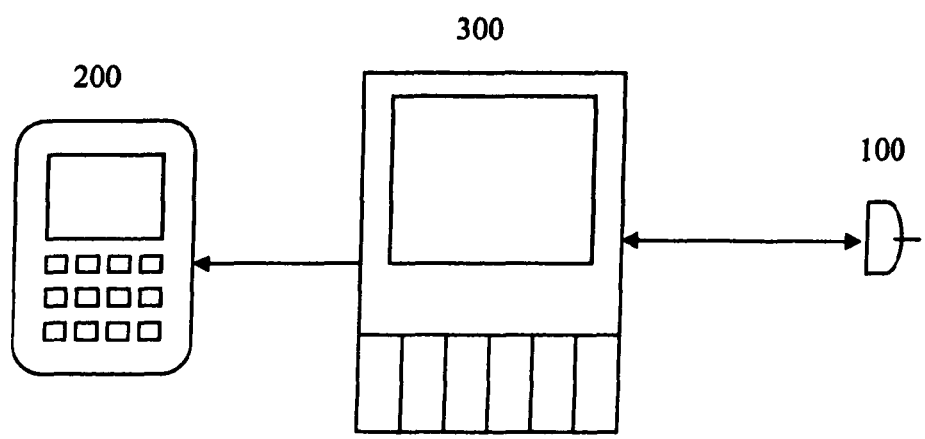
FIG. 1D is a communication flow diagram of a sensor and user interface and auxiliary device in accordance with an embodiment of the present invention.
Figure 1E:
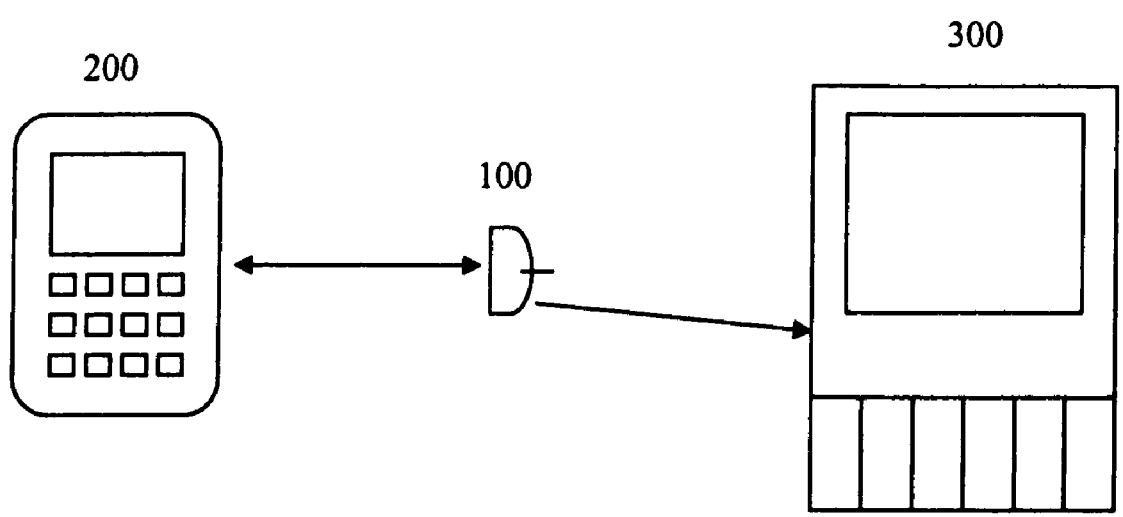
FIG. 1E is a communication flow diagram of a sensor and user interface and auxiliary device in accordance with an embodiment of the present invention.

As shown in FIG. 1D, the sensor 100 may be in communication directly with the auxiliary device 300. The user interface 200 thus may communicate with the auxiliary device 300 which may communicate with the sensor 100. Additionally, as shown in FIG. 1E, the sensor 100 may communicate both with the user interface 200 and with the auxiliary device 300.

Figure 1F:
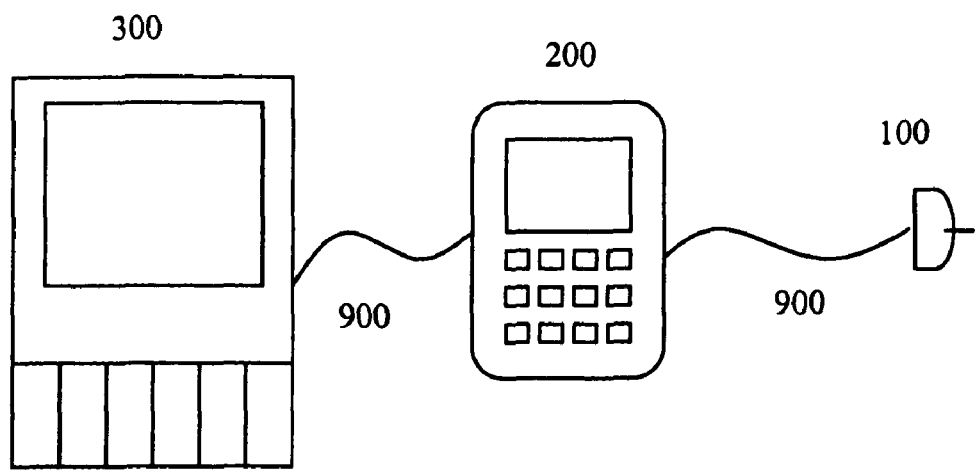
FIG. 1F is diagram of an embodiment of the present invention in accordance with the information flow diagram of FIG. 1B.
Figure 1G:
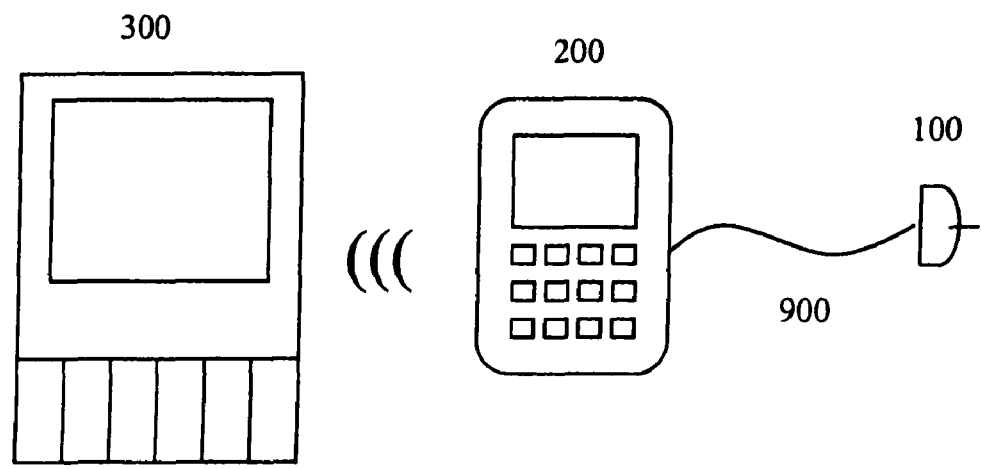
FIG. 1G is diagram of an embodiment of the present invention in accordance with the information flow diagram of FIG. 1B.

FIGS. 1F and 1G illustrate arrangements of embodiments of the present invention in accordance with the data flow of FIG. 1B. As shown in FIG. 1F, the sensor 100 may be tethered to the user interface 200 by a wire 900, and the user interface 200 may be tethered to the auxiliary device 300 by a wire 900. As shown in FIG. 1G, even if the sensor 100 is tethered to the user interface 200 by a wire 900, the user interface 200 may communicate wirelessly with the auxiliary device 300.

Figure 1H:
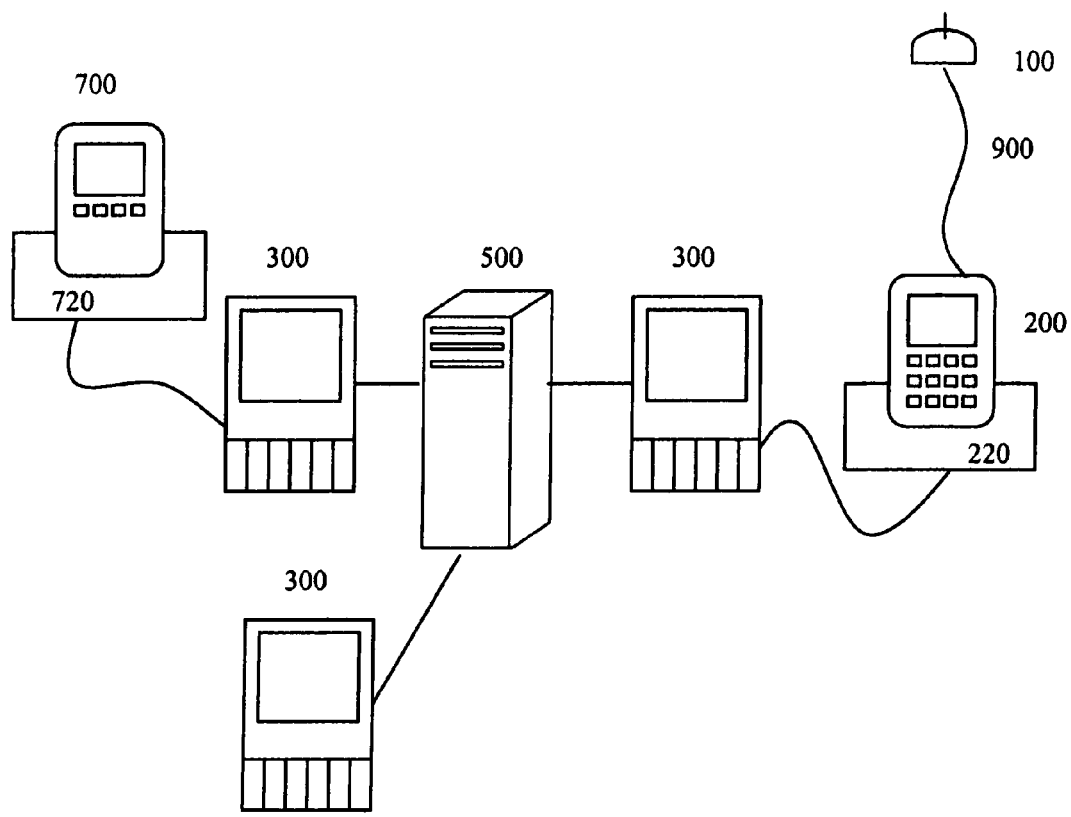
FIG. 1H is diagram of an embodiment of the present invention in accordance with the information flow diagram of FIG. 1C.

One or more of the auxiliary devices may be in communication with a personal computer or server, so that sensor measurements are sent to the personal computer or server. As shown in FIG. 1H, one or more of the auxiliary devices 300 may be in communication with a personal computer or server 500, and blood glucose (BG) reference measurements from a BG meter 700 or a laboratory measurement are sent to the personal computer. Thus, reference measurements may be sent to a personal computer or server 500, and then sent to the user interface 200. These reference measurements may be used for calibration of the sensor data. As shown in FIG. 1H, the user interface 200 may communicate with the personal computer or server 500 through one or more other auxiliary devices 300, such as a patient monitor. The communication with the BG meter 700 and the user interface 200 may also be through one or more of the auxiliary devices 300. Also as shown in FIG. 1H, the user interface 200 may communicate through a docking station 220. The BG meter 700 may also be placed in a docking station 720. The sensor measurements may be stored on a server and made available to one or more PCs. Thus in one example, sensor information can be downloaded to a first PC, the BG meter reference measurements can be downloaded or entered into a second PC, the first PC and the second PC can communicate with each other (such as through a server), the reference measurements can be sent to the user interface, and the sensor measurements and/or reference measurements can be viewed at any of the PCs that are connected to the shared server. One or more devices, such as the user interface and/or the BG meter may use one or more cradles to connect the device to a PC. Alternatively, the reference measurements are sent to a PC, the processed sensor signal is sent to a PC, and the PC calculates the sensor measurements. Alternatively, the user interface may communicate with a personal computer using radio frequency (RF) (not shown). Examples of devices to facilitate communication with the personal computer include, without limitation, communications linking devices such as the ComLink™ sold by Medtronic MiniMed, IR cradles, RF devices, or the like that can be used to send and/or receive signals. For example, the ComLink™ has a transceiver to receive RF signals from a user interface and then forwards received information to the personal computer by wire.

Figure 2A:
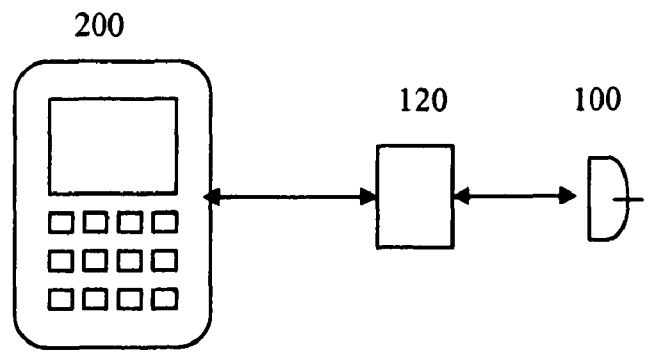
FIG. 2A is an information flow diagram of a sensor, sensor electronics, and user interface in accordance with an embodiment of the present invention.
Figure 2B:
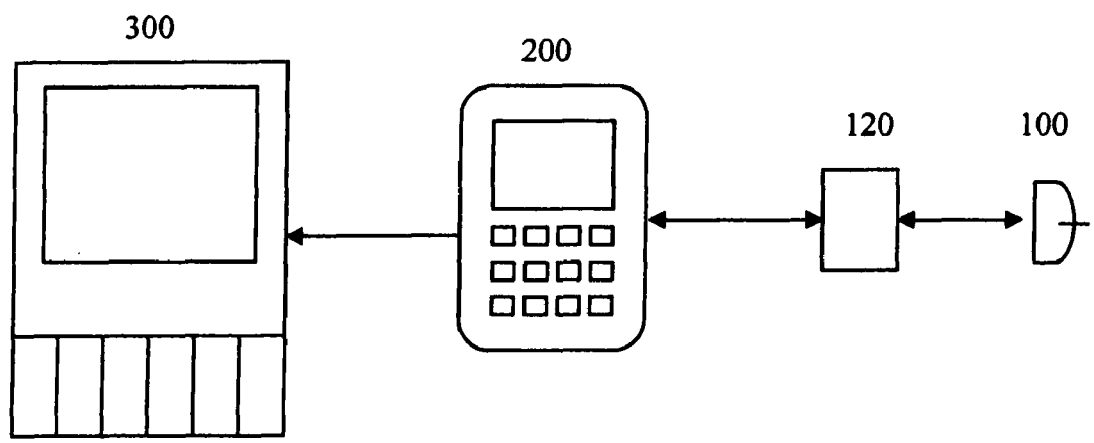
FIG. 2B is an information flow diagram of a sensor, sensor electronics, user interface and display device in accordance with an embodiment of the present invention.
Figure 2C:
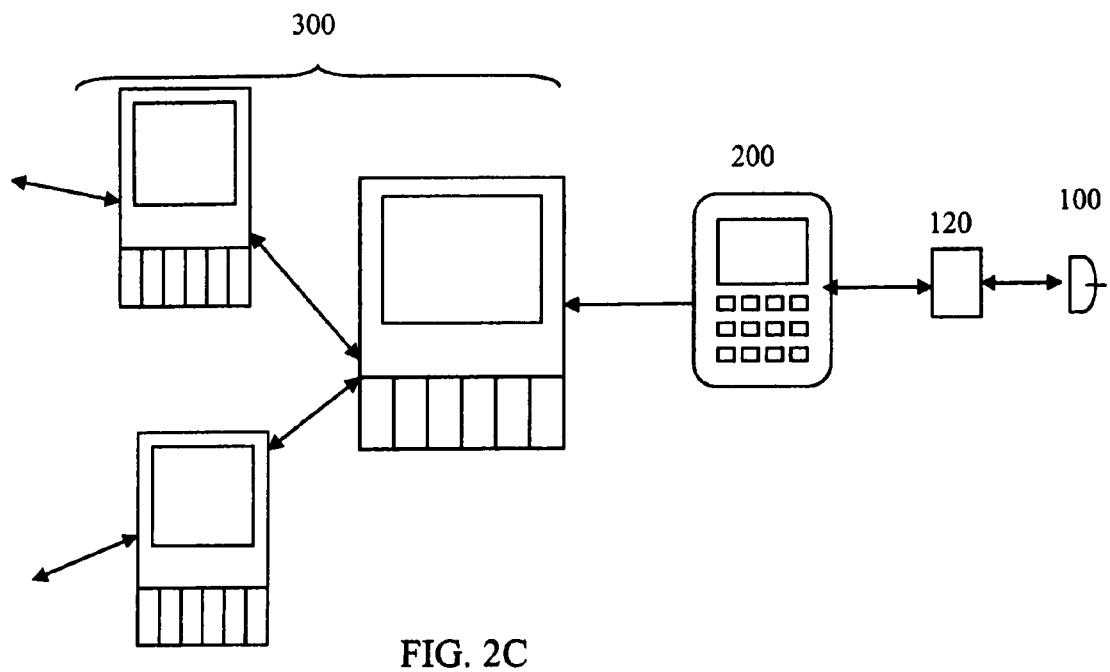
FIG. 2C is an information flow diagram of a sensor, sensor electronics, user interface, and display devices in accordance with an embodiment of the present invention.
Figure 2D:
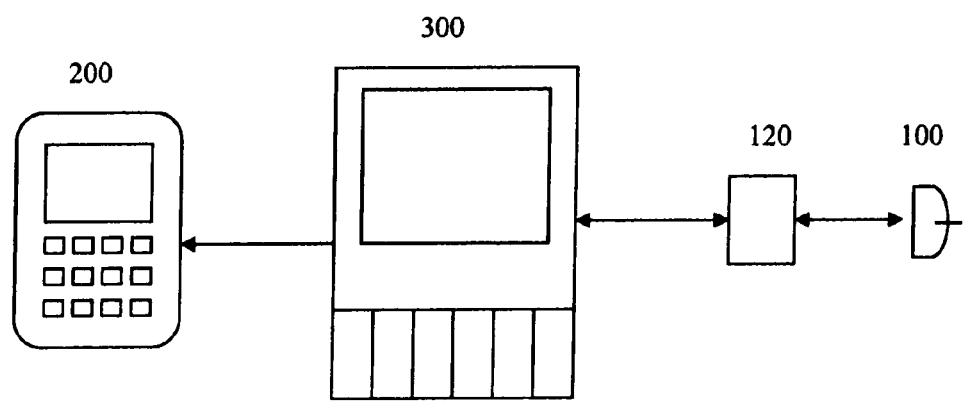
FIG. 2D is an information flow diagram of a sensor, sensor electronics, user interface, and display device in accordance with an embodiment of the present invention.
Figure 2E:
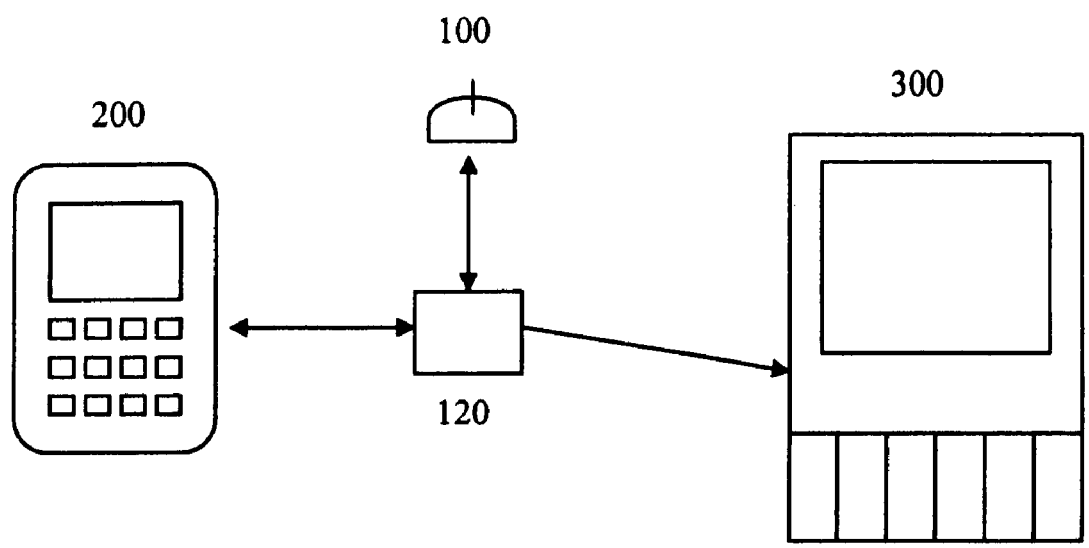
FIG. 2E is an information flow diagram of a sensor, sensor electronics, user interface, and display device in accordance with an embodiment of the present invention.
Figure 2F:
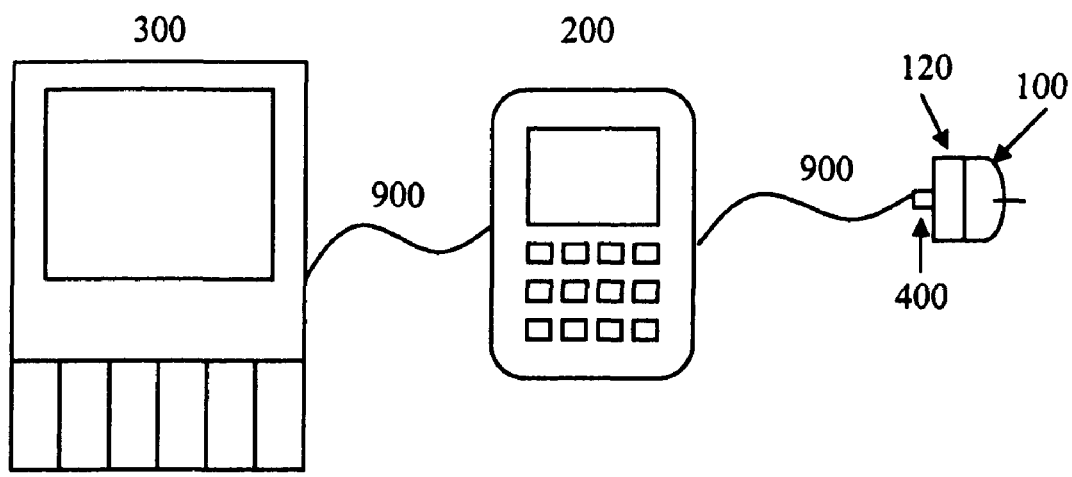
FIG. 2F is diagram of an embodiment of the present invention in accordance with the information flow diagram of FIG. 2B.
Figure 2G:
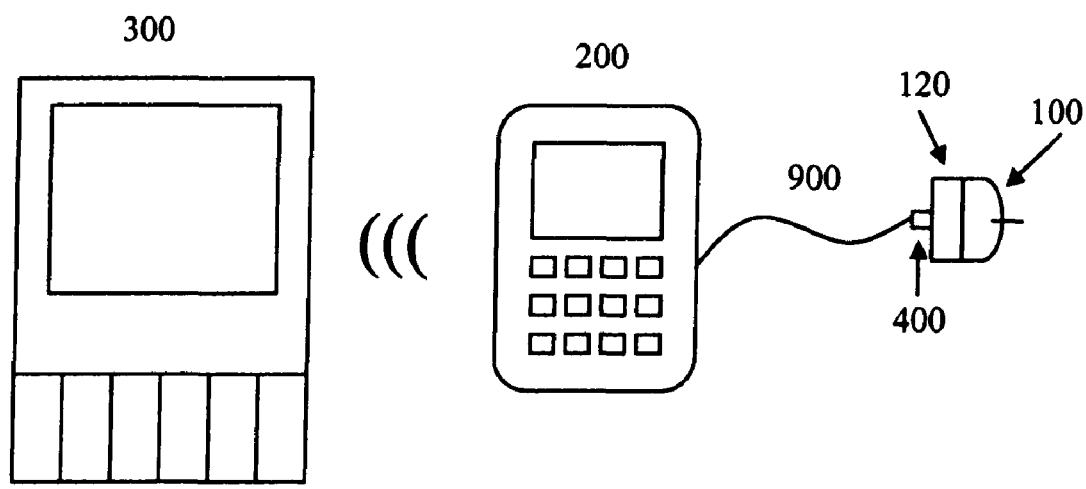
FIG. 2G is diagram of an embodiment of the present invention in accordance with the information flow diagram of FIG. 2B.
Figure 2H:
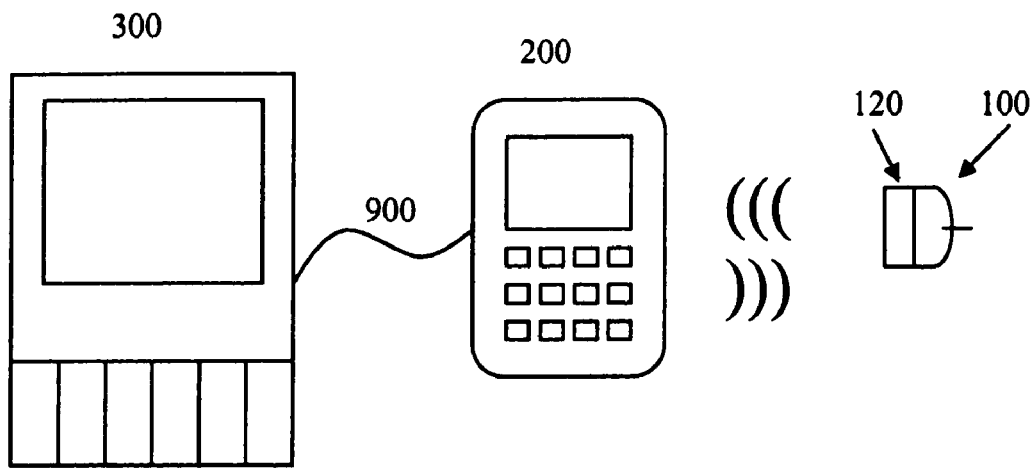
FIG. 2H is diagram of an embodiment of the present invention in accordance with the information flow diagram of FIG. 2B.
Figure 2I:
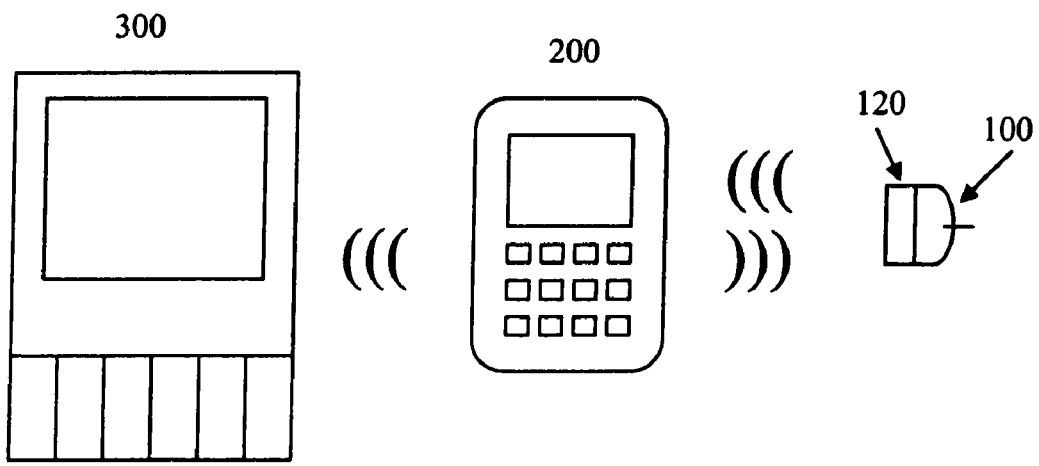
FIG. 2I is diagram of an embodiment of the present invention in accordance with the information flow diagram of FIG. 2B.
Figure 2J:
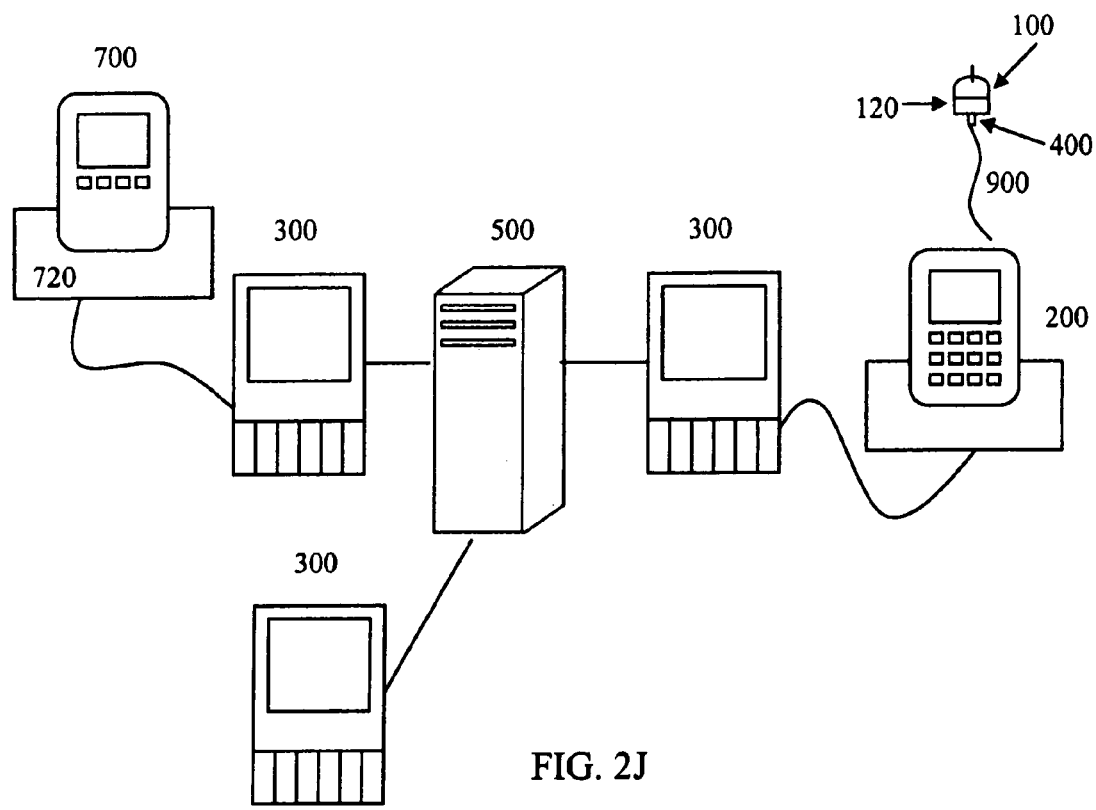
FIG. 2J is diagram of an embodiment of the present invention in accordance with the information flow diagram of FIG. 2C.
Figure 2K:
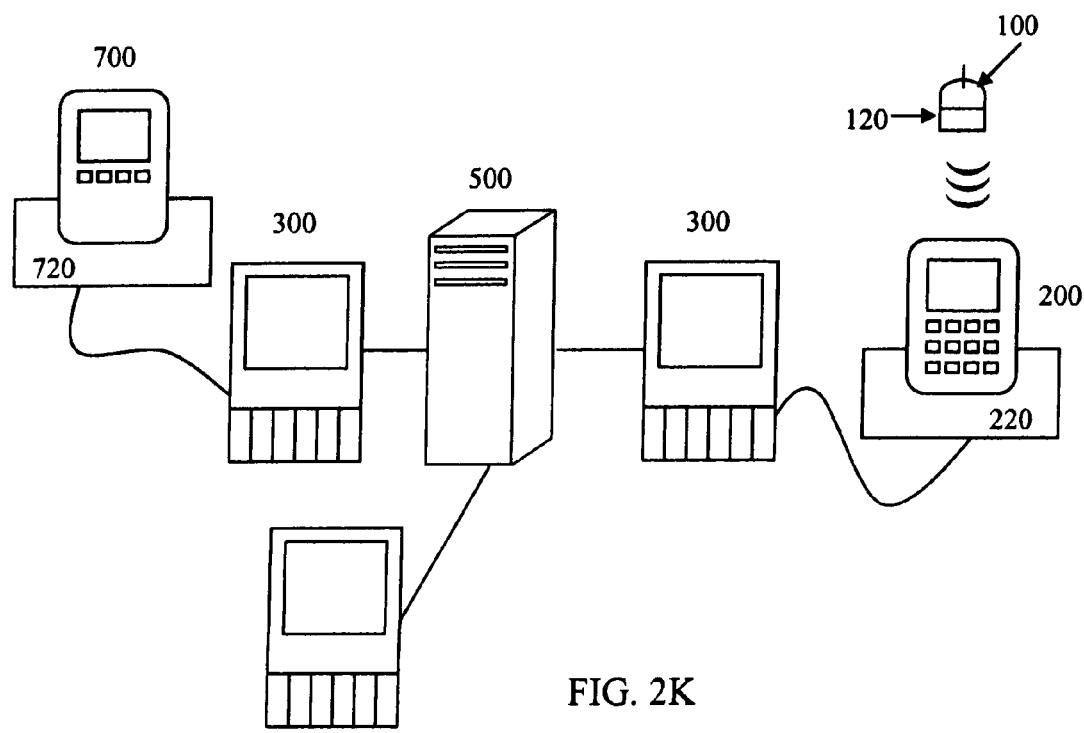
FIG. 2K is diagram of an embodiment of the present invention in accordance with the information flow diagram of FIG. 2C.
Figure 2L:
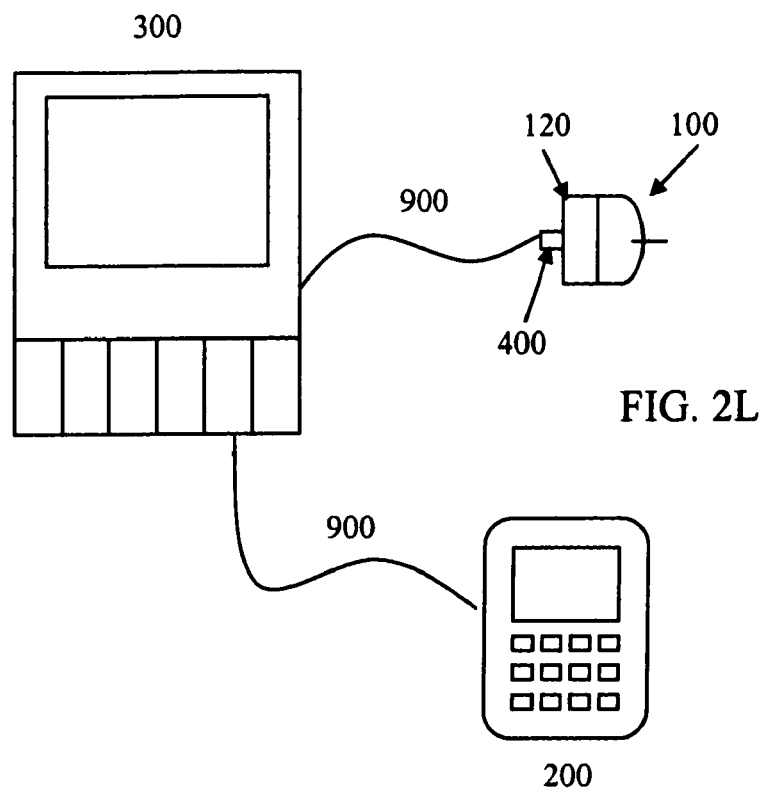
FIG. 2L is diagram of an embodiment of the present invention in accordance with the information flow diagram of FIG. 2D.
Figure 2M:
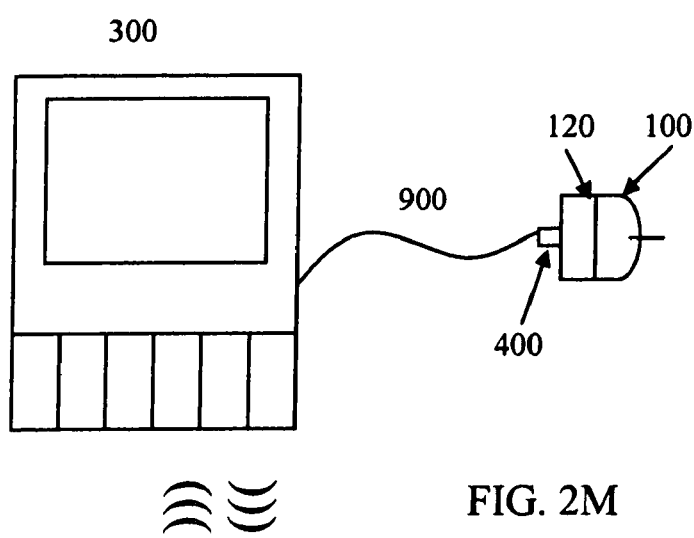
FIG. 2M is diagram of an embodiment of the present invention in accordance with the information flow diagram of FIG. 2D.
Figure 2M:
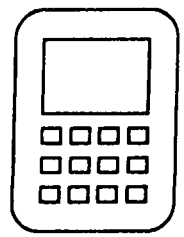
Figure 2N:
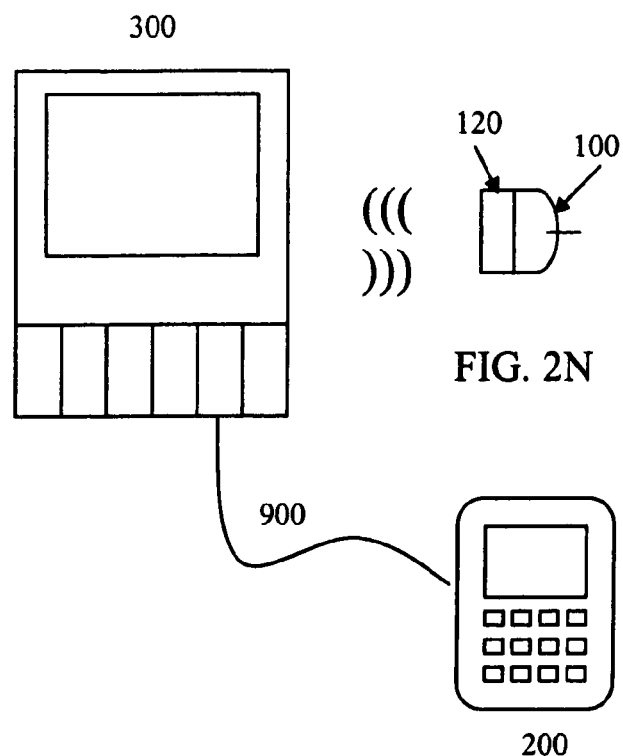
FIG. 2N is diagram of an embodiment of the present invention in accordance with the information flow diagram of FIG. 2D.
Figure 2O:
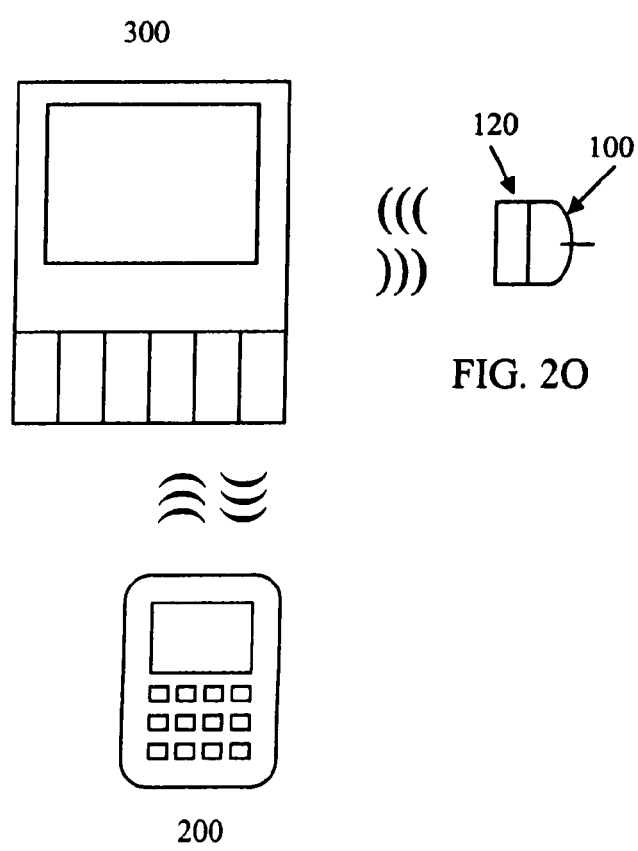
FIG. 2O is diagram of an embodiment of the present invention in accordance with the information flow diagram of FIG. 2D.
Figure 2P:
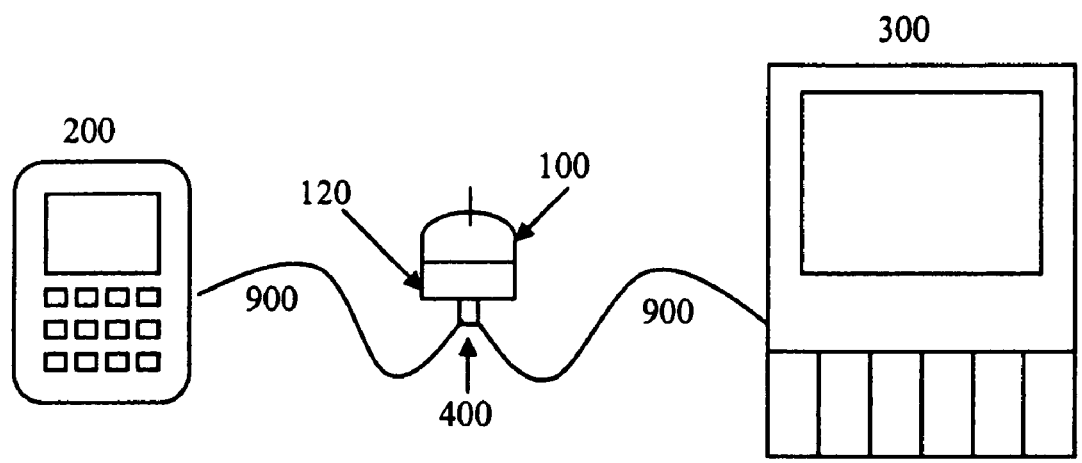
FIG. 2P is diagram of an embodiment of the present invention in accordance with the information flow diagram of FIG. 2E.
Figure 2Q:
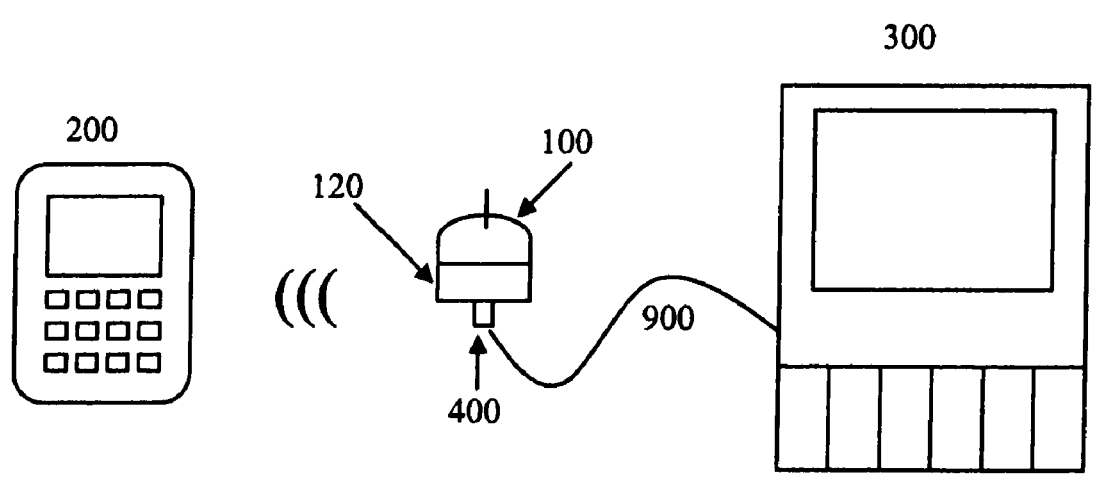
FIG. 2Q is diagram of an embodiment of the present invention in accordance with the information flow diagram of FIG. 2E.
Figure 2R:
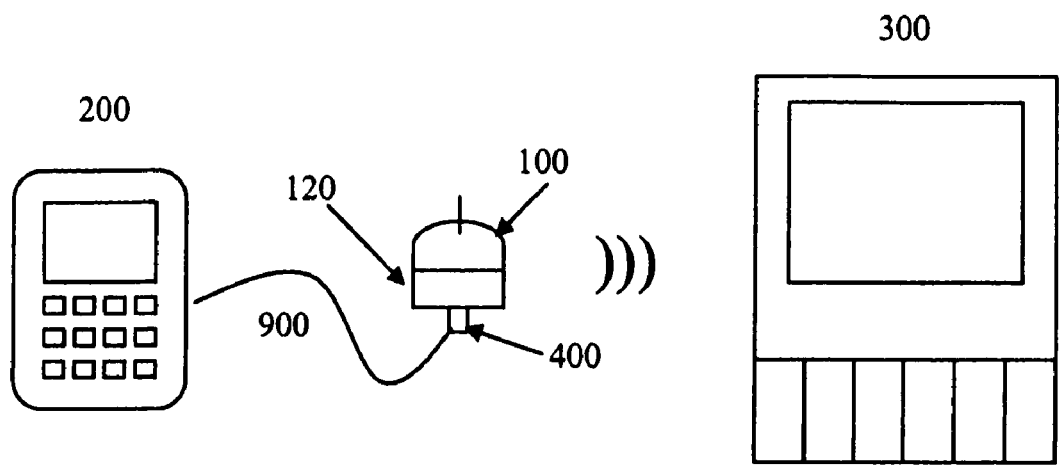
FIG. 2R is diagram of an embodiment of the present invention in accordance with the information flow diagram of FIG. 2E.
Figure 2S:
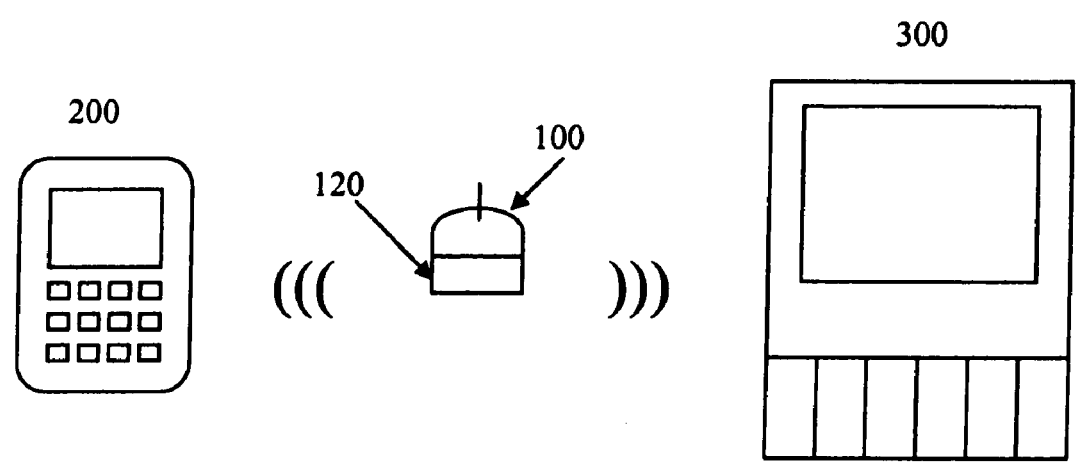
FIG. 2S is diagram of an embodiment of the present invention in accordance with the information flow diagram of FIG. 2E.

FIGS. 2A-2S show data flow of embodiments of the present invention where a sensor communicates with sensor electronics, which communicate to a user interface. The sensor is tethered to sensor electronics, which may communicate over a tethered connection or wirelessly to a user interface and/or auxiliary device. A more detailed discussion of the sensor electronics is included below. As shown in FIG. 2A, a sensor 100 may be in communication with sensor electronics 120, which are in communication with the user interface 200.

In FIG. 2B, the user interface 200 is in communication with one or more auxiliary devices 300, as well as in communication with the sensor electronics 120. As shown in FIG. 2C, the user interface 200 may be in communication with more than one auxiliary device 300. The auxiliary devices 300 may be in communication with each other and/or in communication with the user interface 200 and/or sensor electronics 120.

As shown in FIG. 2D, both the user interface 200 and the sensor electronics 120 may communicate with the auxiliary device 300. And as shown in FIG. 2E, the sensor electronics 120 may be in communication with both the user interface 200 and the auxiliary device 300.

FIGS. 2F-2I, 2L-2O, and 2P-2S are embodiments of the present invention in accordance with the data flow of FIGS. 2B, 2D, and 2E, respectively. They illustrate that the communications between devices may be by wire 900 or may be wireless. In FIGS. 2F and 2G, the sensor 100 and sensor electronics 120 are coupled to each other and to a connector 400. The connector 400 may connect the sensor electronics 120 to a wire 900 that connects to the user interface 200. As shown in FIG. 2F, the user interface 200 may then be tethered to an auxiliary device 300 via a wire 900. As shown in FIG. 2G, the user interface 200 may also be in wireless communication with the auxiliary device 300.

In FIGS. 2H and 2I, the sensor 100 and sensor electronics 120 are coupled to each other but communicate wirelessly to the user interface 200. There need not be a connector in this embodiment, but it is possible to have a sensor and sensor electronics that can communicate through wired or wireless configurations to the user interface. Therefore, the sensor and sensor electronics may be coupled to a wire connector that is not in use when the communication is wireless. In FIGS. 2H and 2I, the sensor 100 is coupled to the sensor electronics 120, which is in wireless communication with the user interface 200. As shown in FIG. 2H, the user interface 200 may then be tethered to an auxiliary device 300 via a wire 900. As shown in FIG. 2I, the user interface 200 may also be in wireless communication with the auxiliary device 300.

In FIGS. 2L and 2M, the sensor 100 and sensor electronics 120 are coupled to each other and to a connector 400. The connector 400 may connect the sensor electronics 120 to a wire 900 that connects to the auxiliary device 300. As shown in FIG. 2L, the auxiliary device 300 may then be tethered to a user interface 200 via a wire 900. As shown in FIG. 2M, the auxiliary device 300 may also be in wireless communication with the user interface 200.

In FIGS. 2N and 2O, the sensor 100 and sensor electronics 120 are coupled to each other but communicate wirelessly to the auxiliary device 300. In FIGS. 2N and 2O, the sensor 100 is coupled to the sensor electronics 120, which is in wireless communication with the auxiliary device 300. As shown in FIG. 2N, the auxiliary device 300 may then be tethered to a user interface 200 via a wire 900. As shown in FIG. 2O, the auxiliary device 300 may also be in wireless communication with the user interface 200.

In FIGS. 2P, 2Q and 2R, the sensor 100 and sensor electronics 120 are coupled to each other and to a connector 400. The connector 400 may couple the sensor electronics 120 to one or more wires 900 that connects to the auxiliary device 300 and/or the user interface 200. As shown in FIG. 2P, sensor electronics 120 may be coupled to both auxiliary device 300 and user interface 200 via wires 900. As shown in FIG. 2Q, the sensor electronics 120 may be coupled to the auxiliary device 300 via wire 900 and in wireless communication with the user interface 200. As shown in FIG. 2R, the sensor electronics 120 may be coupled to the user interface 200 via wire 900 and in wireless communication with the auxiliary device 300. In FIG. 2S, the sensor 100 is coupled to the sensor electronics 120, which is in wireless communication with the auxiliary device 300 and with the user interface 200.

One or more of the auxiliary devices may be a personal computer or server, and sensor measurements may be sent to the personal computer or server. Additionally, blood glucose (BG) reference measurements from a BG meter or a laboratory measurement may be sent to the personal computer or server, and then may be sent to the user interface. As shown in FIGS. 2J and 2K, the user interface 200 may communicate with a personal computer 500, and a BG meter 700 may communicate with the personal computer 500. Also as shown in FIGS. 2J and 2K, the user interface 200 may communicate with the personal computer or server 500 through one or more other auxiliary devices 300, such as a patient monitor. The communication with the BG meter 700 and the user interface 200 may also be through one or more of the auxiliary devices 300. The user interface 200 may communicate through a docking station 220. The BG meter 700 may also be placed in a docking station 720. In FIG. 2J the sensor 100 is coupled to the sensor electronics 120, which is coupled to a connector 400 for coupling the sensor electronics 120 to the user interface through a wire 900. As shown in FIG. 2K, the communication between the sensor electronics 120 (coupled to the sensor 100) and the user interface 200 may also be wireless. The sensor information may be stored on a server and made available to one or more personal computers. Thus in one example, sensor information can be downloaded to a first personal computer, the BG meter reference measurements can be downloaded or entered into a second personal computer, the first personal computer and the second personal computer can communicate with each other (such as through a server), the reference measurements can be sent to the user interface, and the sensor measurements and/or reference measurements can be viewed at any of the personal computers that are connected to the shared server. Alternatively, the reference measurements may be sent to a personal computer, the processed sensor signal may be sent to a personal computer, and the personal computer may then calculate the sensor measurements.

As discussed above, the present invention may include electrical components. For example, the electrical components may include one or more power supplies, regulators, signal processors, measurement processors, reference memories, measurement memories, user interface processors, output devices, and input devices. The one or more power supplies provide power to the other components. The regulator supplies regulated voltage to one or more sensors, and at least one of the one or more sensors generates a sensor signal indicative of the concentration of a physiological characteristic being measured. Then the signal processor processes the sensor signal generating a processed sensor signal. Then the measurement processor calibrates the processed sensor signal using reference values from the reference memory, thus generating sensor measurements. Then the measurement memory stores sensor measurements. Finally, the sensor measurements are sent to the user interface processor, which forwards the sensor measurements to an output device.

The one or more power supplies may be a battery. Alternatively, the one or more power supplies may be one or more batteries, a voltage regulator, alternating current from a wall socket, a transformer, a rechargeable battery, or the like. The regulator may be a voltage regulator. Alternatively, the regulator may be a current regulator, or other regulator. The source of power for operating the sensor or for charging a battery within sensor electronics may include an AC power source (e.g., 110-volt or 220-volt), DC power source (e.g., a 12-volt DC battery), or pulsating DC power source (e.g., a power charger that provides pulsating DC current to a battery that re-energizes the battery and removes the lead sulfate deposits from the plates).

The signal processor may perform one or more functions such as, converting the sensor signal from an analog signal to a digital signal, clipping, summing, filtering, smoothing, and the like.

The measurement processor may perform one or more functions such as, but not limited to, calibrating (converting the processed sensor signal into measurements), scaling, filtering, clipping, summing, smoothing, analyzing, and the like. The measurement processor may also analyze whether the sensor is generating signals indicative of a physiological characteristic or whether the sensor is no longer functioning properly. For example, the measurement processor may detect that the processed sensor signal is too high, too low, changes too rapidly, or is too noisy for a properly functioning sensor, and thus indicate that the sensor should be replaced. The measurement processor may further analyze whether to generate an alarm due to a characteristic of the sensor measurement, such as the sensor measurement is too high, too low, increasing too rapidly, decreasing too rapidly, increasing too rapidly given its present value, decreasing too rapidly given its present value, too high for a given duration, too low for a given duration, and the like. Additionally, the measurement processor may estimate the remaining battery life.

The reference memory may contain one or more reference values for converting the processed sensor signal into a sensor measurement. For example, 1 micro-amp (µamp) equals 40 milligrams of glucose per deciliter of fluid (mg/dl), or 2 nano-amps equals 10 millimoles of glucose per liter of fluid (mmol/l). Reference measurements are input into the input device periodically during the life of the sensor, with each reference measurement paired with a processed sensor signal, and each pair of a reference measurement with a processed sensor signal stored in the reference memory as a reference value. Thus, the measurement processor may use new reference values to convert the processed sensor signal into sensor measurements. Alternatively, the reference values may be factory installed. Thus no periodic reference measurements are needed. Additionally, the reference memory may contain both factory installed reference values and periodic reference values.

The user interface processor may transfer sensor measurements from the measurement memory to the output device. The user interface processor may also accept inputs from the input device. If the sensor includes a memory, the user interface may send parameters from the inputs to the sensor for storage in the memory. The inputs may include one or more of certain setup parameters, which it may be possible to change later but may be fixed: one or more high thresholds, one or more low thresholds, one or more trend rates, alarm acknowledge, minimum time between alarms, snooze duration, sensor serial number, codes, identification numbers (ID), password, user name, patient identification, reference measurements, and the like. The user interface processor may also tell the output device what to do including one or more of the following: display the latest sensor measurement, display the latest reference measurement, display a graph of sensor measurements, display thresholds, activate an alarm, display a message such as an alarm message, an error message, a command, an explanation, a recommendation, a status, and the like. Additionally, the user interface processor may perform one or more processing or analyzing functions such as, calibrating, scaling, filtering, clipping, summing, smoothing, calculating whether the sensor is generating signals indicative of a physiological characteristic or whether the sensor is no longer functioning properly, estimating remaining battery life, determining whether to generate an alarm due to a characteristic of the sensor measurement, and the like.

If one or more electrical components reside in the same device, then one or more of the electrical components may be combined into a single electrical component, such as combining the user interface processor, measurement processor and the signal processor; or combining the measurement memory and the reference memory. Alternatively, the components may be independent despite in which device they reside.

It is possible that a sensor will need to receive regulated power for a defined duration before it can generate a stable signal, in other words it must warm up. And, if regulated power is removed from the sensor, the sensor must warm up again when the power is restored before measurements can be used. Alternatively, it is possible that each time the sensor is warmed up, new reference measurements must be input and paired with a processed sensor signal to create new reference values, which are stored in the reference memory. Reference values are needed to calibrate the processed sensor signal into sensor measurements. Furthermore, periodic reference values may be needed, and if a stable (warmed up) processed sensor signal is not available when a new reference values is needed, then a new reference measurement may have to be collected when the processed sensor signal is available and stable. In the mean time the processed sensor signal cannot be used to generate a sensor measurement. In other words, if it is time for a new reference measurement to maintain calibration and the sensor signal is not available to pair with the new reference measurement, then the sensor loses calibration and will have to be recalibrated when the sensor signal becomes available. It is also possible that more than one reference value will need to be collected before the sensor measurement is considered calibrated.

There is a possibility, particularly in a hospital environment, that the sensor may be disconnected from the user interface and/or from the patient monitor for extended periods of time. For example, patients are moved between rooms and beds regularly when the may not be connected to any patient monitor (e.g. a surgery patient may move from admission to surgery to recovery, and so forth). In some cases, calibration will be scheduled at particular intervals. When the sensor, coupled to sensor electronics, is disconnected from the user interface and/or patient monitor, one of these intervals may occur. For such a situation, it is useful to have a way to calibrate the sensor and sensor electronics while separated from the user interface and/or patient monitor. For example, the sensor may include a blood glucose (BG) meter to support calibration. The BG meter may be display-free to, for example, reduce excess size and weight. The BG meter included in the sensor would then provide reference values for calibration to the sensor electronics. It is also possible to couple the sensor electronics to a BG meter or to use a wireless connection to the BG meter to receive the reference values.

Figure 3A:
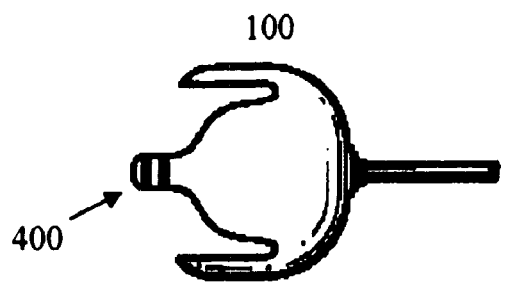
FIG. 3A shows a sensor in accordance with an embodiment of the present invention.
Figure 3B:
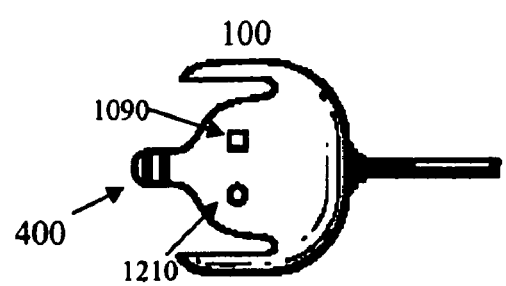
FIG. 3B shows a sensor with incorporated electronics in accordance with an embodiment of the present invention.
Figure 3C:
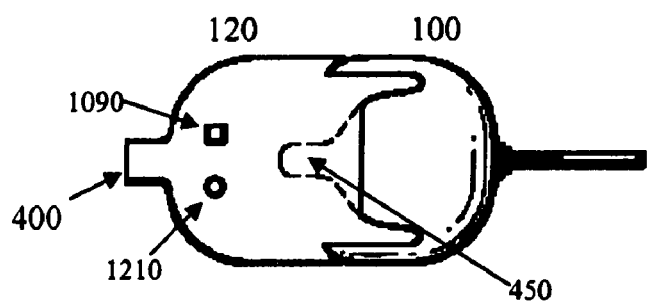
FIG. 3C shows a sensor connected with a previously separate sensor electronics that includes a wire for connecting to another device in accordance with an embodiment of the present invention.
Figure 4A:
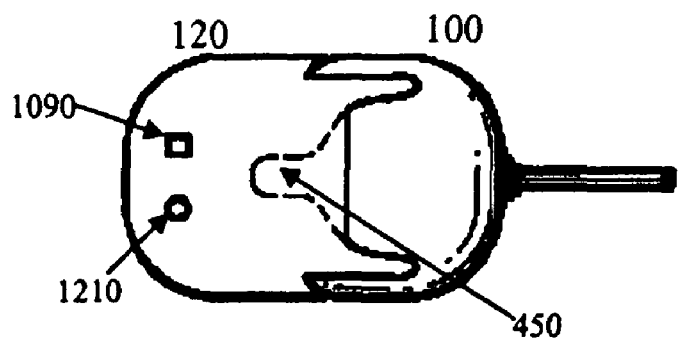
FIG. 4A shows a sensor connected to a previously separate sensor electronics including a transmitter in accordance with an embodiment of the present invention.
Figure 4B:
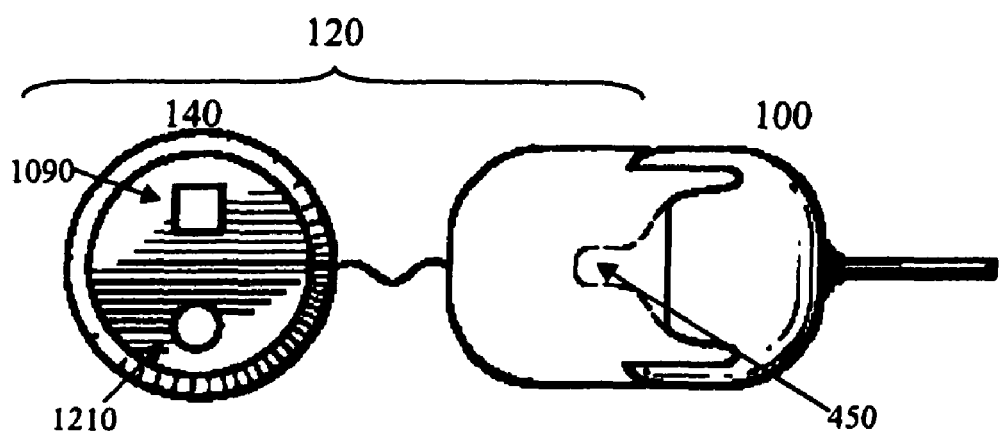
FIG. 4B shows a sensor connected to a previously separate sensor electronics including a transmitter in accordance with an embodiment of the present invention.

FIGS. 3A-3C and 4A-4C illustrate physical embodiments of aspects of the present invention. FIGS. 3A-3C show sensors with and without sensor electronics with connectors 400, so that they may be wired to one or more devices. In the embodiments shown in FIGS. 1A-1H, discussed above, there is a connector 400 between the sensor 100 and a device, which is not shown. FIG. 3A illustrates a simple sensor in accordance with the invention as embodied in FIGS. 1A-1H. The sensor 160 includes the connector 400. The sensor 100 is not always wired to a device. For example, as shown in FIGS. 3C, 4A, and 4B, the sensor 100 shown in FIG. 3A may be coupled to sensor electronics. In this particular embodiment, however, the sensor 100 does not include sensor electronics.

There are a number of ways to include sensor electronics in the sensor of the present invention. As shown in FIG. 3B, the sensor 100 may include a connector 400 and the sensor electronics may be a monolithic part of the sensor. In FIG. 3B, electrical components, specifically the regulator 1090 and sensor power supply 1210, are shown directly on the sensor 100. Alternatively, the sensor electronics 120 may be coupled to the sensor 100 by a connector 450, such as shown in FIG. 3C. The sensor electronics 120 in FIG. 3C include one or more electrical components, such as the regulator 1090 and sensor power supply 1210 and may be wired to one or more devices through connector 400.

Figure 4C:
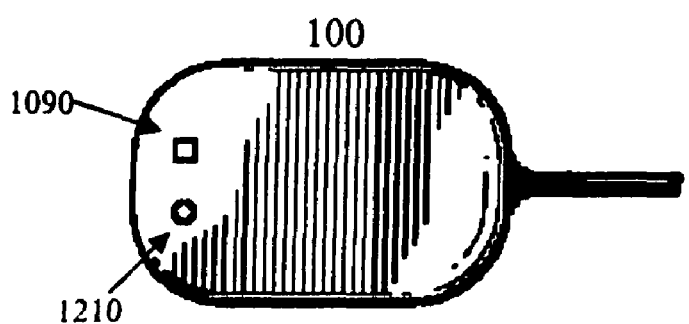
FIG. 4C shows a sensor and electronics encased in a housing which includes a transmitter in accordance with an embodiment of the present invention.

FIGS. 4A-4C show sensors which are intended to be used for wireless communication with one or more devices. As shown in FIG. 4A, the sensor 100 may be coupled to the sensor electronics 120 by a connector 450. The sensor electronics 120 may include one or more electrical components, such as the regulator 1090 and sensor power supply 1210. As shown in FIG. 4B, the sensor may be coupled to a sensor electronics 120 that include a portion coupled to the sensor via a connector 450 and wired to a separate portion 140, which includes sensor electronics. Although the sensor electronics are shown as having electrical components on only one portion, it is possible to have some electrical components on one portion of the sensor electronics and other electrical components on another portion. Embodiments shown in FIG. 4B are discussed in more detail in U.S. patent application Ser. No. 09/465,715, filed Dec. 17, 1999, which is herein incorporated by reference. As shown in FIG. 4C, the sensor electronics may be a monolithic part of the sensor 100.

Many different wireless communication protocols may be used. Some protocols are for one-way communication and others are for two-way communication. For one-way communication, the transmitting device may have a transmitter and the receiving device may have a receiver. For two-way protocols, each device typically has a transceiver, but each device could have a transceiver and a receiver. For any wireless embodiment, a transceiver may be used in place of a receiver or a transmitter, because the transceiver can perform like a receiver or a transmitter or both.

Where the sensor electronics 120 (wired or wireless) are separated from the sensor 100 by a connector 450, such as shown in FIGS. 3C, 4A, and 4B, the sensor electronics may first become powered by the sensor power supply at the-time that the sensor electronics are attached to the sensor. Thus, the sensor power supply shelf life is increased. Alternatively, the sensor electronics may always be powered. The sensor electronics may be powered by the sensor power supply when triggered by other means, such as when the user interface is connected to the sensor electronics, when a magnetic switch is triggered, when a mechanical switch is triggered, or the like.

The duty cycle of the sensor power supply may vary based on the sensor electronics being connected or disconnected from the user interface and/or patient monitor. For example, when the sensor electronics are disconnected, the duty cycle may be reduced (e.g., by using fewer electrical components, by decreasing data acquisition, and the like), which will allow for a greater sensor power supply shelf life. If the sensor and sensor electronics lose power for a prolonged period of time, the calibration process may have to be repeated. The sensor electronics may include circuitry to detect low battery levels and may be coupled to an alarm that will activate if the low battery level reaches a certain threshold.

FIGS. 5A-5H are block diagrams of the electronic components of embodiments of aspects of the present invention. In the embodiment shown in FIG. 5A, the user interface 200 is tethered to the sensor 100. The tether may be interrupted by a connector 400 so that the sensor 100 and the user interface 200 can be separated. The sensor 100 does not include a power supply in FIG. 5A. When the patient disconnects a sensor from the user interface 200, then the sensor no longer receives power from the regulator and thus may require time to warm up again and may require re-calibration when re-connected with the user interface.

The user interface power supply 1030 supplies power to the user interface 200 and may also supply power to the sensor 100. The regulator 1090 supplies regulated voltage to sensor 100, and the sensor 100 generates a sensor signal indicative of the concentration of a physiological characteristic being measured. Then the signal processor 1080 processes the sensor signal generating a processed sensor signal. Then the measurement processor 1070 calibrates the processed sensor signal using reference values from the reference memory 1050, thus generating sensor measurements. Then the measurement memory 1060 stores sensor measurements. Finally, the sensor measurements are sent to the user interface processor 1040, which forwards the sensor measurements to an output device 1010. The reference values, and other useful data, may be input through an input device 1020.

Figure 5A:
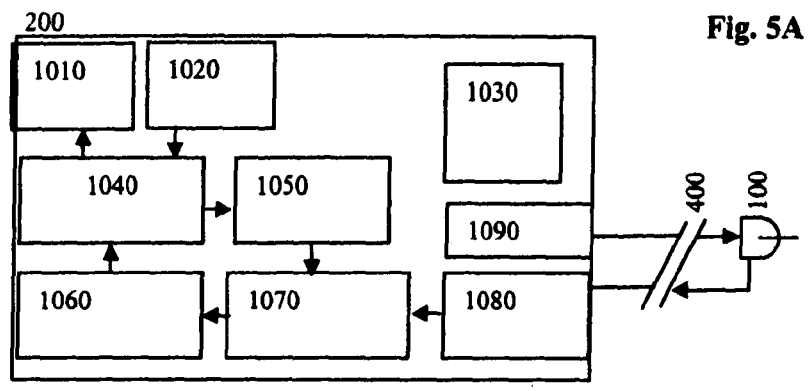
FIG. 5A is a block diagram of a user interface and sensor in accordance with an embodiment of the present invention.
Figure 5B:
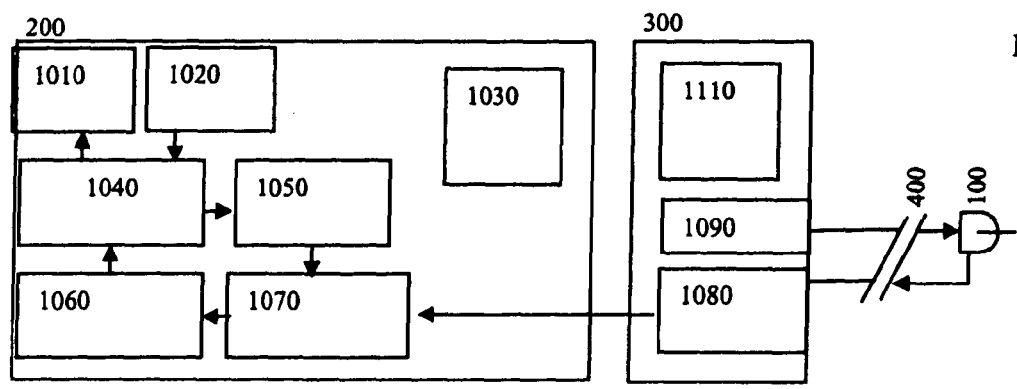
FIG. 5B is a block diagram of a user interface, auxiliary device and sensor in accordance with an embodiment of the present invention.

As shown in FIG. 5B, an auxiliary device 300 may be tethered to the sensor 100, and the tether may be interrupted by a connector 400 so that the sensor 100 and the user interface 200 can be separated. Thus, a patient wearing a sensor does not have to remain tethered to a device, such as a user interface or an auxiliary device. The user can wear the sensor and temporarily or permanently disconnect from other devices. This can be useful if the patient needs to leave the proximity of one or more devices. For example, the sensor may be tethered to a stationary device such as a wall-mounted or bed-mounted display, and the patient must leave the room for a therapeutic procedure. As shown in FIG. 5B, the auxiliary device may include an auxiliary device power supply 1110, regulator 1090 and the signal processor 1080, so that the auxiliary device processes the sensor signal.

In the above embodiments, where the sensor does not include a power supply, when the sensor is disconnected from the other devices, the sensor no longer receives power. The tether includes one or more wires to carry the regulated voltage to the sensor and carry the sensor signal to the signal processor. For particular types of sensors, the sensor must be warmed up again when re-connected with the user interface. Where the reference memory is included in the user interface, one or more reference values may be periodically measured and stored in the reference memory when they are collected. If the sensor is disconnected from the user interface when a new reference value is required, however, the sensor will need calibration when it is re-connected.

One or more devices other than the sensor may be in communication with each other, such as discussed above in reference to FIGS. 1B-1H. The one or more devices other than the sensor, such as an auxiliary device and a user interface, may share a tethered connection such as a wire. As used herein the term "wire" means and includes any physical conductor capable of transmitting information by non-wireless means including, for example, one or more conventional wires, a serial or parallel cable, a fiber optic cable, and the like. The term "wire" also includes any physical conductor capable of carrying regulated voltage, electrical power, and the like. Additionally, the tethered connections may include at least one connector so that at least one device can be separated from the others. One or more of the one or more devices other than the sensor, such as an auxiliary device and a user interface, may communicate wirelessly, such as RF, IR, sub-sonic, and the like communications, such as shown in FIG. 1G.

Alternatively, the user interface may be coupled to sensor electronics, which may be coupled to the sensor, such as shown in FIGS. 5C-5H. If a power supply and regulator stay with the sensor (as part of the sensor electronics), when the sensor is disconnected from the user interface, then the sensor can remain powered and retain calibration. Thus, the sensor may not require warm up time and may not require re-calibration when re-connected to the same user interface that it was connected to previously.

The sensor power supply may be a battery capable of operating for at least the entire life of the sensor. For example, the life of the sensor may be, for example, about 2 days, 3 days, 4 days, 5 days, 7 days, 10 days, 20 days, 30 days, 45 days, 60 days, a year, and the like. Alternatively, the life of the sensor may be shorter than 2 days, such as, about 36 hours, 30 hours, 24 hours, 12 hours, 6 hours, 3 hours and the like. The sensor power supply may be rechargeable. For example, the sensor power supply may be recharged when the sensor electronics are connected to the user interface. Additionally, the sensor power supply may be sized to last the entire duration that the sensor electronics are disconnected from the user interface, such as 15 minutes, 30 minutes, 1 hour, 2 hours, 3 hours, 4 hours, 6 hours, 8 hours, 12 hours, 24 hours, and the like. The sensor power supply may include one or more of a transformer, capacitor, power cell, solar cell, replaceable battery, and the like. Alternatively, the sensor power supply is a replaceable battery.

Figure 5C:
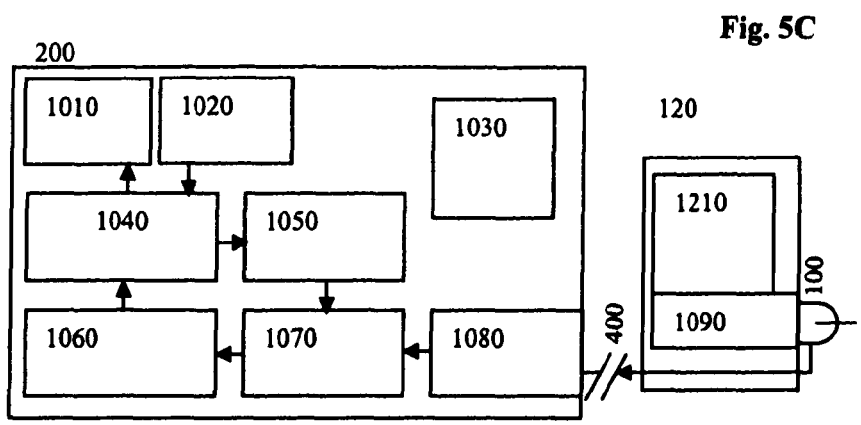
FIGS. 5C and 5D are block diagrams of a user interface, sensor and sensor electronics in accordance with embodiments of the present invention.

In the embodiment shown in FIG. 5C, the sensor electronics 120 include a sensor power supply 1210 and regulator 1090. Thus, when the sensor 100 is disconnected from the user interface 200, the sensor 100 remains powered. Because the sensor electronics do not include memory storage, the sensor data is not saved while the sensor 100 is not connected to the user interface 200.

Figure 5D:
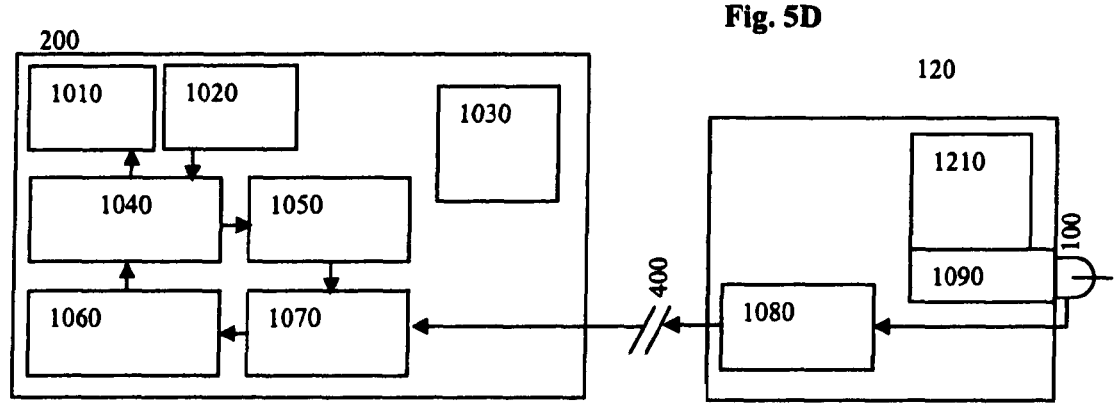
Figure 5E:
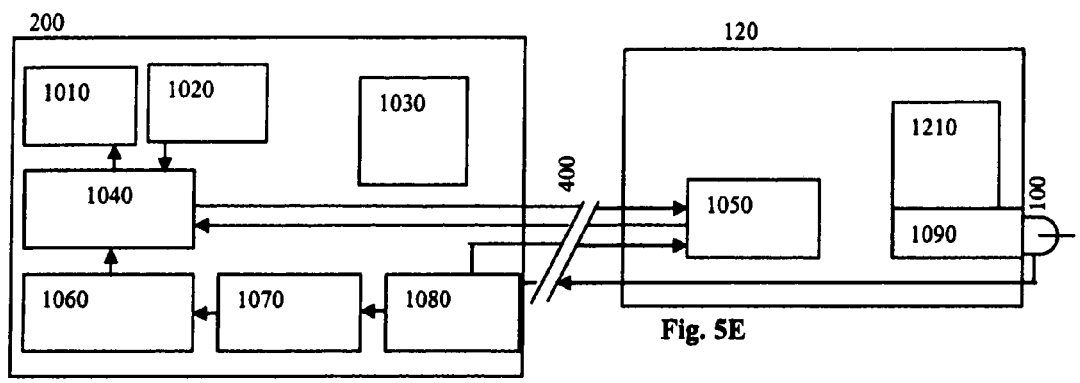
FIGS. 5E and 5F are block diagrams of a user interface, sensor and sensor electronics in accordance with embodiments of the present invention.

As shown in FIG. 5E, it is possible to transport reference values with the sensor 100 so that the reference values are kept with the sensor 100 even when the sensor 100 is no longer connected to the user interface 200. In this embodiment, a sensor power supply 1210 and regulator 1090 and reference memory 1050 are included in the sensor electronics 120 that stay with the sensor 100 when disconnected from the user interface 200 at connector 400. When the sensor 100 is disconnected from the user interface 200, the sensor 100 may remain powered and retain calibration. Thus, the sensor 100 does not require re-calibration when re-connected. Furthermore, the sensor 100 may be connected to a different user interface and remain calibrated, because the calibration values are carried along with the sensor 100 and can be sent to the different user interface. If BG meter readings are needed for calibration, they are entered into the user interface 200 and sent to the reference memory 1050 in the sensor electronics 120. If BG meter readings are not needed, then the reference memory 1050 may contain factory installed reference values for the sensor. In the particular embodiment shown in FIG. 5E, sensor data is not collected while the sensor 100 is not connected to a user interface.

Figure 5F:
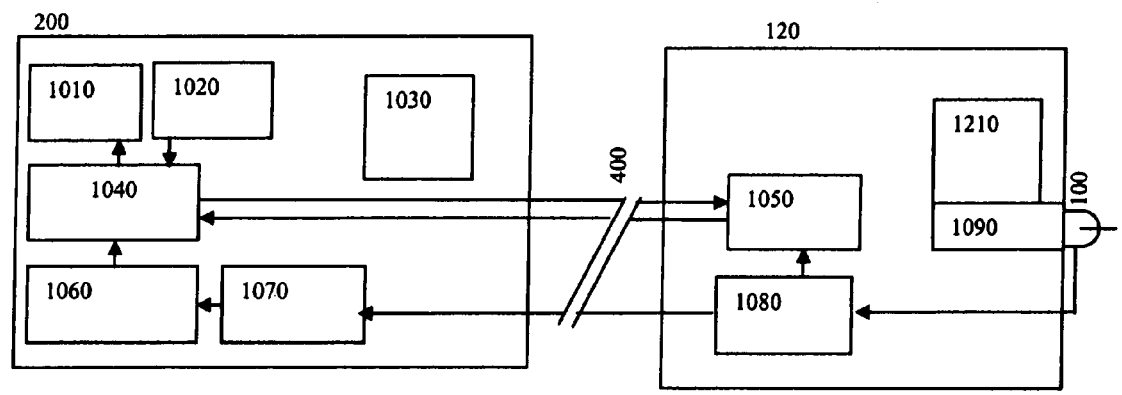

As shown in FIGS. 5D and 5F, the sensor electronics 120 may include a signal processor 1080. The signal processor simplifies communication across the tethered connection because the signal processor can convert weak analog sensor signals (which might be especially sensitive to noise) into digital signals, which can be made highly resistant to noise. Often, wires behave like antennas and gather radio frequency signals and the like, thus adding noise to signals carried on the wires.

Figure 5G:
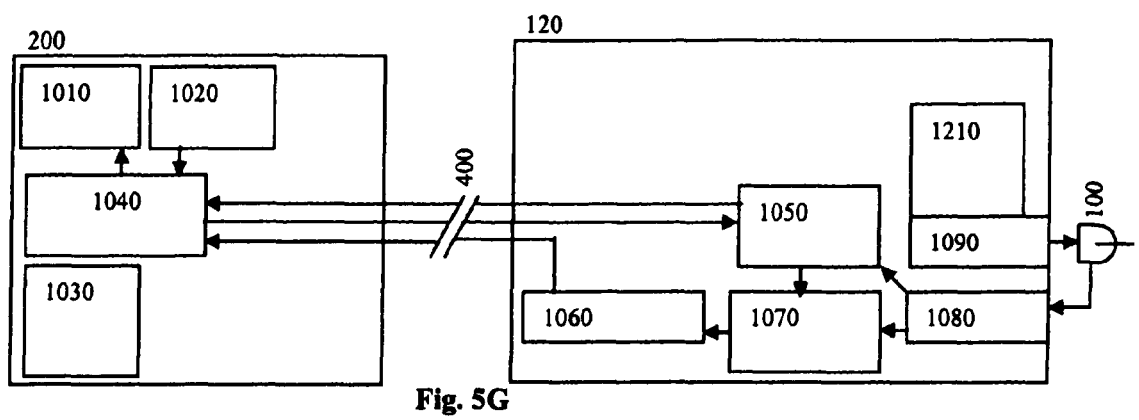
FIG. 5G is a block diagram of a user interface, sensor and sensor electronics in accordance with an embodiment of the present invention.

As shown in FIGS. 5E-5H, the user interface 200 may be tethered to the sensor electronics 120, and the sensor electronics 120 may include a reference memory 1050. One or more reference values may be periodically measured, entered into the user interface 200 and transferred to the reference memory 1050, as shown in FIGS. 5E and 5G. If the sensor 100 is disconnected from the user interface 200 when a new reference value is required, the sensor 100 will need calibration when it is re-connected. As shown in FIGS. 5E and 5G, the power supply 1210, regulator 1090 and reference memory 1050 may be included with the sensor electronics 120. If the sensor 100 is disconnected from the user interface 200, the sensor 100 remains powered and retains calibration. Thus, the sensor does not require re-calibration or warm up when re-connected. Furthermore, the sensor may be disconnected from a first user interface and then connected to a second user interface and remain calibrated because the calibration values are carried along with the sensor and can be sent to the second user interface.

As shown in FIG. 5E, and 5F, the sensor electronics 120 includes the reference memory 1050, sensor power supply 1210 and regulator 1090, but does not include the measurement memory 1060. Since the measurement memory 1060 is not included with the sensor electronics 120, the sensor data is not collected while the sensor 100 is not connected to a user interface. Furthermore, if periodic reference measurements are required, and the sensor electronics 120 are disconnected from the user interface 200 at the time that a new reference measurement is needed, then the sensor 100 will lose calibration, and a new reference measurement will be needed when the sensor electronics 120 are reconnected to a user interface.

As shown in FIG. 5G, the sensor electronics 120 may include the reference memory 1050, sensor power supply 1210, regulator 1090, signal processor 1080, measurement processor 1070, and the measurement memory 1060. Since the measurement memory 1060 is included with the sensor electronics 120, the sensor data is collected even while the sensor 100 is not connected to a user interface. Thus, a patient wearing a sensor may move about freely while disconnected from the user interface, and when they reconnect, all of the sensor data can be sent to the user interface for analysis and display. If however, periodic reference measurements are required, and the sensor electronics are disconnected from the user interface at the time that a new reference measurement is needed, then the sensor may lose calibration, and a new reference measurement will be needed when the sensor electronics are reconnected to a user interface.

Figure 5H:
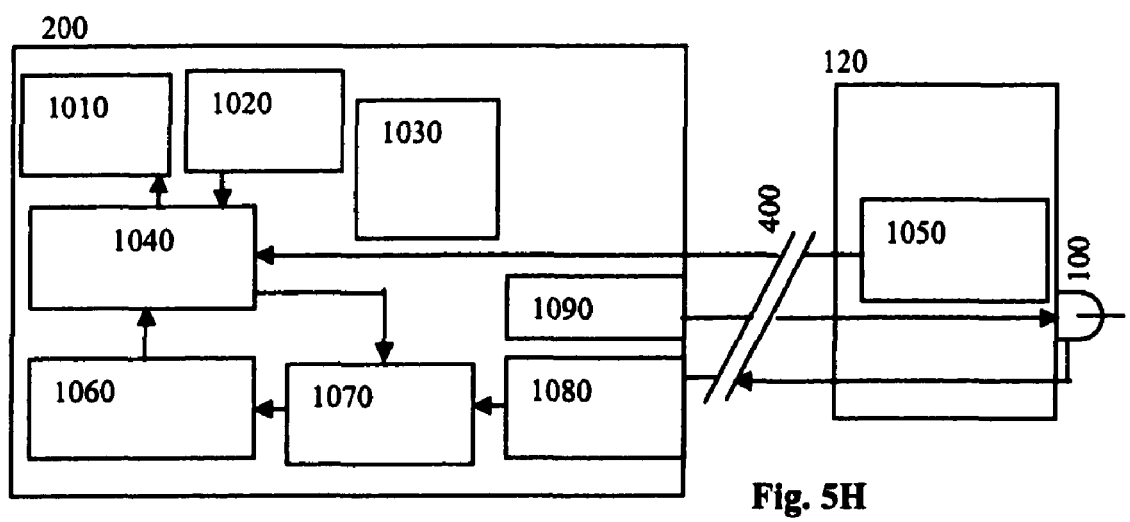
FIG. 5H is a block diagram of a user interface, sensor and sensor electronics in accordance with an embodiment of the present invention.

Periodic reference values may not be required. One or more reference values may be stored in the reference memory at the factory. Furthermore, the reference memory may be non-volatile such as a flash memory, and therefore not require power to maintain the reference values as shown in FIG. 5H. Thus, reference values might be factory installed with each sensor and no power is required to maintain the reference values in the reference memory. As shown in FIGS. 5E, 5F, 5G and 5H, the reference memory 1050 may be included in the sensor electronics 120. Thus, a sensor may be disconnected from a user interface and connected to a second and not require calibration. The sensor may, however, require a warm up period if it loses power when disconnected from a user interface as shown in FIG. 5H.

Alternatively, one or more factory installed reference values may be stored in volatile memory with each sensor, and power is required to maintain the reference values in memory as shown in FIGS. 5E, 5F and 5G. The reference memory and a sensor power supply may optionally be included in the sensor electronics. Thus, a sensor may be disconnected from a user interface and connected to a second and not require calibration and the sensor may not require a warm up period if it does not lose power when disconnected from a user interface.

The tether may include one or more wires or one or more fiber optic cables or the like. Alternatively, the tether may not include a wire or cable or the like if the sensor electronics includes a sensor power supply and a regulator, and thus a wire is not needed to carry power to the sensor.

As shown in FIGS. 6A-6E, and as discussed above with respect to FIGS. 2A-2S and 4A-4C, the sensor electronics 120 may include a mechanism for wireless communication 1205, such as a radio frequency (RF) transmitter or transceiver, or an infrared (IR) transmitter or transceiver, light emitting diode (LED), sonic transmitter such as a speaker, and the like. Sensor electronics that include wireless communication capability are a subset of all sensor electronics and are referred to as wireless sensor electronics. Thus, a sensor may be physically coupled to wireless sensor electronics and establish a wired connection between the wireless sensor electronics and the sensor, but the wireless sensor electronics and sensor are not tethered to a user interface or an auxiliary device. Thus, a user can wear the sensor and move about freely, physically disconnect from other devices. This can be useful if the patient needs to leave the proximity of one or more devices. For example, if the patient is wearing a sensor with wireless sensor electronics that communicate with a stationary device such as a wall-mounted or bed-mounted display, then the patient may leave the room for a therapeutic procedure without having to disconnect the sensor electronics from any devices. Communication between the sensor electronics and one or more devices may be interrupted and may be re-established later. For example, the sensor electronics may be temporarily moved out of range for RF communication with a wall mounted device, or may be temporarily misaligned for IR communication with one or more devices.

The sensor wireless communication mechanism may be a processor that handles the communication protocol and manages transferring information in and out of the reference memory and the measurement memory. The measurement memory may contain one or more of calibrated measurements, time and dates associated with measurements, raw un-calibrated measurements, diagnostic information, alarm history, error history, settings and the like. Settings may be determined by a user using a keypad on the user interface, and the settings are sent to a memory in the sensor electronics. Additionally, the sensor wireless communication mechanism may be a processor that evaluates the calibrated measurements according to user defined settings and sends results of the evaluation to the user interface. For example, the user may set an alarm threshold, which is sent to be stored in a memory in the sensor electronics. Then the sensor wireless communication mechanism compares a calibrated measurement to the alarm threshold and if the calibrated measurement exceeds the alarm threshold, the communication system sends an alarm message to the user interface. Finally, the user interface displays the alarm message.

The alarms may function even when the sensor and sensor electronics are disconnected from the user interface and/or patient monitor. In this way, the patient will be warned if he/she becomes hyperglycemic or hypoglycemic, even when not connected to the user interface and/or patient monitor. For example, the sensor electronics may be coupled to an alarm. As discussed above, an alarm threshold may be stored in a memory in the sensor electronics. If a calibrated measurement exceeds the alarm threshold, the alarm coupled to the sensor electronics may be activated. Similarly, if a battery is low on power, or the sensor is not performing properly, or communication with another device has been lost, or an error has occurred, or a warning is needed, then the sensor electronics may activate an alarm. The alarm may be an audible alarm, a visible alarm, a tactile alarm (such as a vibrating alarm), or any combination thereof. In particular embodiments, the sensor electronics includes one or more components for alarming a user.

User defined parameters such as alarm thresholds, minimum time between alarms, alarm snooze time, trend alarm thresholds, patient ID, one or more identifying codes, a password, and the like may be sent from the user interface to the sensor electronics and stored in memory in the sensor electronics. Thus, settings that are established for a particular patient are not lost when the patient is moved to a new location and the sensor electronics establishes communication with a second user interface. The user defined settings are sent to the second user interface when communication is first established with sensor electronics. Each set of sensor electronics may have a unique ID, code, name, serial number, or the like, which is sent to the user interface so that the user interface can identify which sensor electronics it is communicating with. The unique ID for a sensor electronics may be required to be entered into a user interface before the user interface will recognize communications from a sensor electronics. Thus, if a user interface detects communication from more than one sensor electronics, then user interface can determine which signal to respond to based on the unique ID contained in the communications. Furthermore, the user interface and/or auxiliary devices may have one or more unique IDs so that each device, user interface, and sensor electronics can determine whether to accept communications from each other. For example, a patient monitor may be programmed to accept communications from a user interface or sensor electronics as long as the communication includes a unique ID representing a particular sensor. Thus, if two patients share a room and transmissions from a first patient's sensor electronics are received by a second patient's user interface and/or patient monitor, the second patient's user interface and/or patient monitor will ignore the communication. Yet, the first patient's user interface and/or patient monitor will accept the communication from the first patient's sensor electronics. In another example, a user interface ID number is entered into a patient monitor, and the patient monitor will only accept communications that contain the user interface ID number.

Figure 6A:
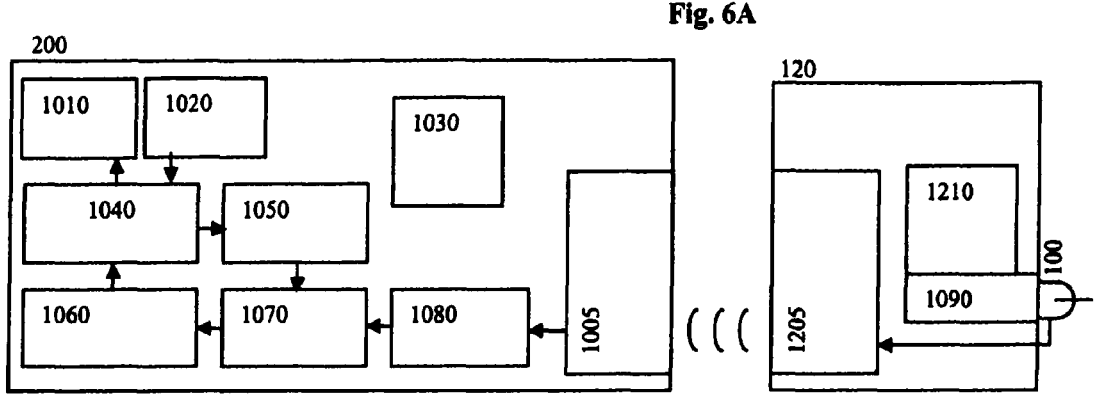
FIGS. 6A and 6B are block diagrams of a user interface, sensor and sensor electronics in accordance with embodiments of the present invention.
Figure 6B:
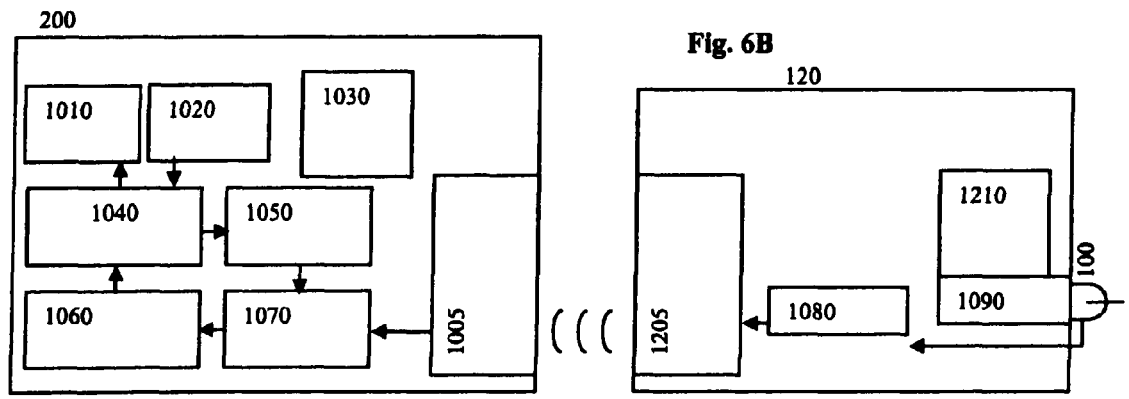
Figure 6C:
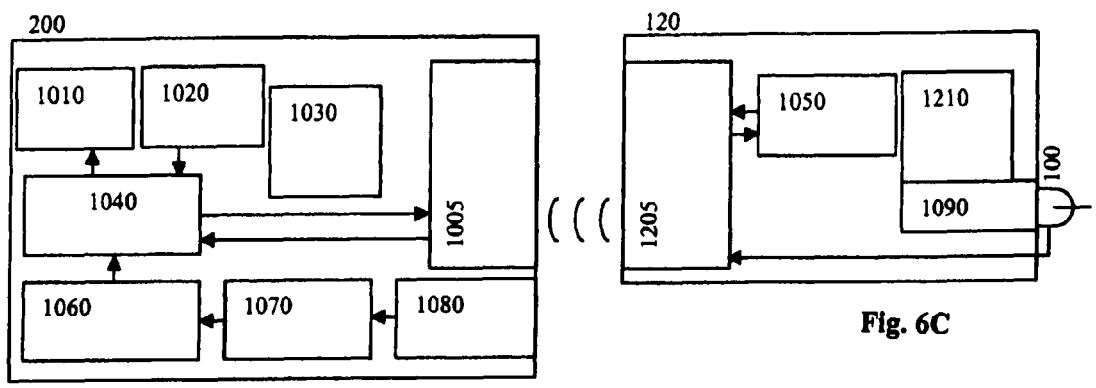
FIGS. 6C and 6D are block diagrams of a user interface, sensor and sensor electronics in accordance with embodiments of the present invention.

FIGS. 6A-6E show similar embodiments to FIGS. 5A-5H. However, as shown in FIGS. 6A-6C, the sensor electronics 120 include sensor wireless communication mechanism 1205 and the user interface 200 includes user interface wireless communication mechanism 1005. As shown in FIG. 6A, the sensor power supply 1210 and regulator 1090 are part of the sensor electronics 120. Thus, the sensor 100 constantly remains powered. As shown in FIG. 6B, the signal processor 1080 may reside in the sensor electronics 120, so that the sensor 100 can remain powered but can also perform processing. In particular embodiments, if the signal processor 1080 includes an analog to digital converter. Thus, digital communication can be used to send the processed sensor signal to the user interface 200.

Once the sensor is powered and warmed up by the sensor power supply and the regulator, the sensor remains powered and sufficiently warmed up and thus does not need to warm up again no matter how many different devices it communicates with. One or more reference values may be measured periodically and stored in the reference memory when they are collected. If the wireless sensor electronics cannot establish communication with user interface when a new reference value is required, the sensor will need calibration when communication is re-established.

Figure 6D:
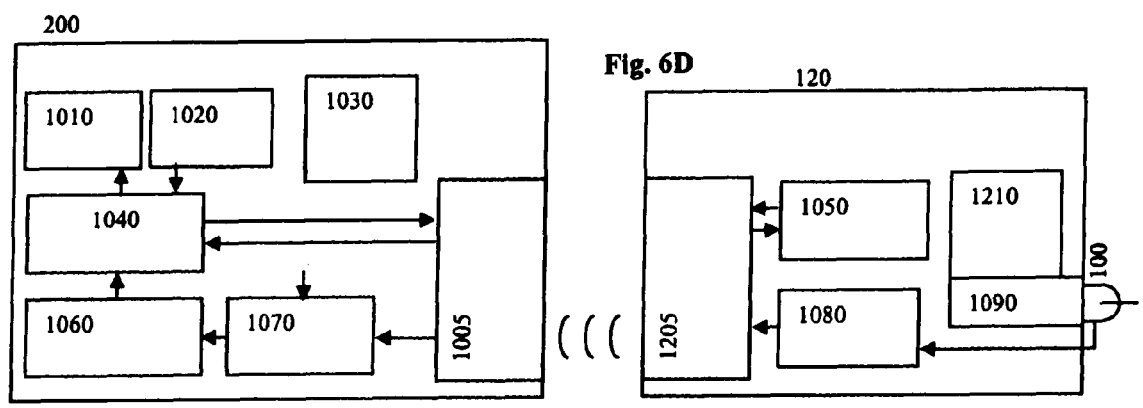

As shown in FIG. 6C, the sensor power supply 1210, regulator 1090 and reference memory 1050 may stay with the sensor 100. Then if the sensor 100 loses communication with the user interface 200 (such as because the patient walks too far away from the user interface), then the sensor remains powered and retains calibration. Thus, the sensor 100 does not require re-calibration or warm up time when it re-establishes communication with the user interface 200. Furthermore, the sensor 100 may establish communication with a second user interface and remain calibrated because the calibration values are carried along with the sensor 100 and can be sent to the second user interface. As shown in FIG. 6D, the wireless sensor electronics may include the reference memory 1050, sensor power supply 1205, regulator 1090, signal processor 1080 and a wireless communication mechanism 1205, but does not include the measurement memory 1060. Since the measurement memory is not included with the wireless sensor electronics, the sensor data is not collected while the wireless sensor electronics is not in communication with a user interface. Furthermore, if periodic reference measurements are required, and communication cannot be established between the wireless sensor electronics and the user interface at the time that a new reference measurement is needed, then the sensor will lose calibration, and a new reference measurement will be needed when the wireless sensor electronics and a user interface have established communication.

Figure 6E:
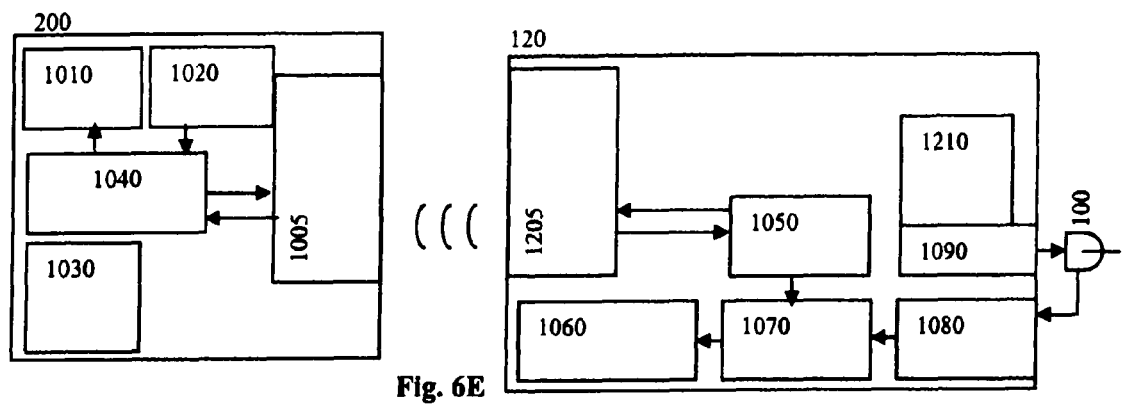
FIG. 6E is a block diagram of a user interface, sensor and sensor electronics in accordance with an embodiment of the present invention.

As shown in FIG. 6E, in addition to the sensor power supply 1210, regulator 1090, reference memory 1050, the measurement memory 1070 and measurement processor 1060 may stay with the sensor 100. When communication is lost between the sensor electronics 120 and the user interface 200, the sensor 100 remains powered, retains calibration and collects and stores measurements. Thus, the sensor 100 does not require re-calibration or warm up when communication is established with any user interface. A patient wearing a sensor may move about freely, and when the wireless sensor electronics establishes communication with a user interface all of the sensor data can be sent to the user interface for analysis and display. If however, periodic reference measurements are required, and the wireless sensor electronics and user interface cannot establish communication at the time that a new reference measurement is needed, then the sensor may lose calibration, and a new reference measurement will be needed when the wireless sensor electronics are in communication with a user interface.

Alternatively, periodic reference values are not required. One or more reference values may be stored in the reference memory at the factory. Furthermore, the reference memory may be non-volatile such as a flash memory, and therefore not require power to maintain the reference values. Thus, reference values might be factory installed with each sensor and no power would be required to maintain the reference values in the reference memory. The reference memory may be included in the wireless sensor electronics. Thus, calibration would not be required when the sensor electronics establishes communication with a user interface.

Alternatively, one or more factory installed reference values may be stored on a volatile reference memory in wireless sensor electronics that are included with each sensor. In this case, power could be needed to maintain the reference values in memory. Alternatively, the reference memory and a sensor power supply are included in the wireless sensor electronics.

If the reference values are factory installed, they may be included on a CD, floppy disk, or other removable storage devices. If the reference values are stored on a CD, for example, they may be downloaded into a personal computer and then downloaded into the user interface and/or sensor electronics. The reference values may also be stored on a removable or non-removable non-volatile memory. For example, if the reference values are stored on a removable non-volatile memory, the memory may be included in a flash memory card. The flash memory card may be adapted to be used in the user interface and/or the sensor electronics. The reference values may be stored on a non-volatile or volatile memory that is included with the sensor electronics at the factory. In this case, if the memory included with the sensor electronics is volatile, the sensor electronics should include a power source so that the sensor electronics may retain the reference values during shipping and storage. One set of sensor electronics may contain reference values to calibrate a number of sensors. For example, if a sensor electronics is shipped with a number of sensors, the reference values may calibrate all of those sensors.

Figure 7:
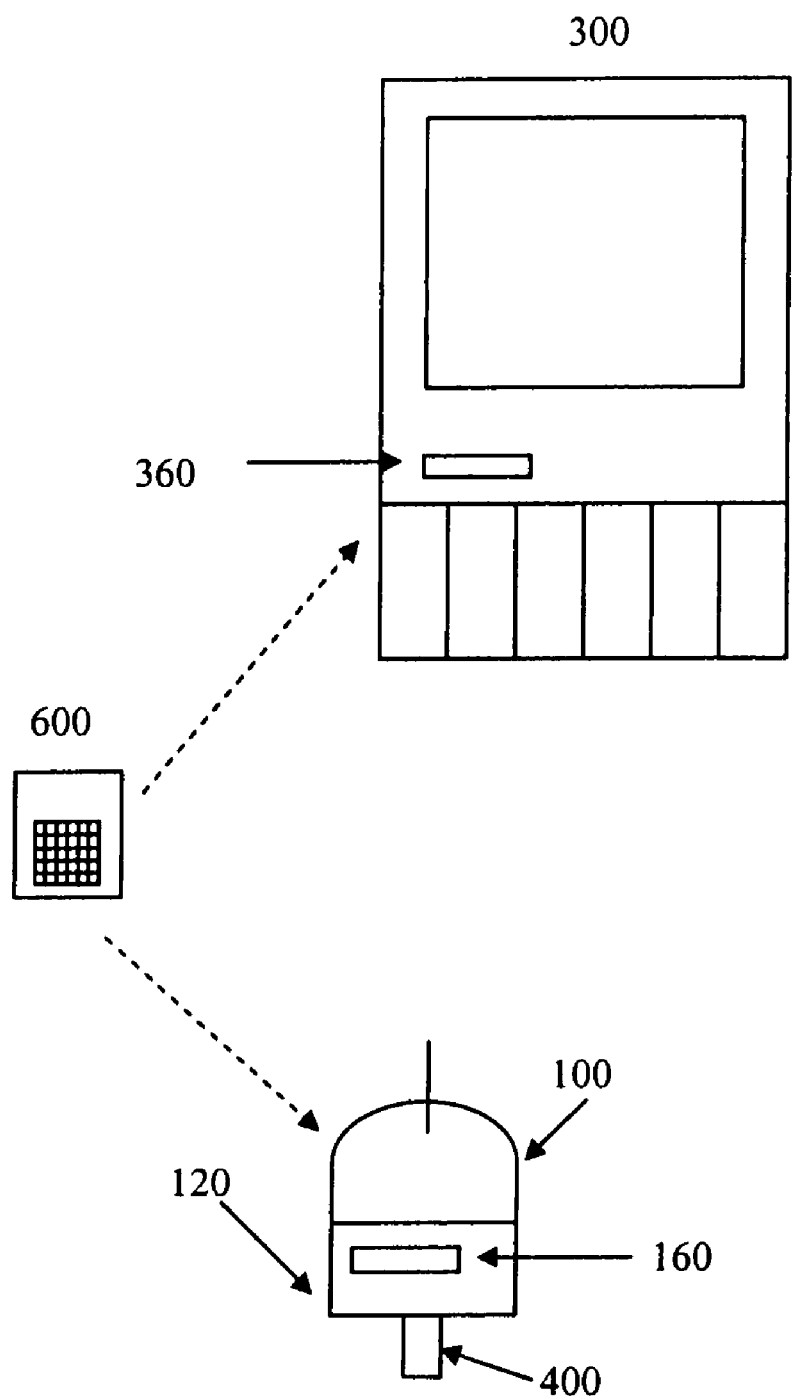
FIG. 7 shows a sensor and sensor electronics, user interface, and flash memory card in accordance with an embodiment of the present invention.

As shown in FIG. 7, the user interface 200 and/or the sensor electronics 120 may include a slot 260, 160 for a flash memory card 600. The flash memory card 600 may include reference values that are factory input or reference values that are input later. Additionally, the flash memory card 600 may store additional desired data. The flash memory card 600 may be included when the user interface 200 and/or sensor electronics 120 is shipped from a factory or reseller. Or, the flash memory card 600 may be purchased separately for use with the user interface 200 and/or the sensor electronics 120. Additionally, a flash memory card may be used in the patient monitor.

As noted above with respect to FIGS. 6C, 6D, and 6E, the wireless sensor electronics 120 may include a reference memory 1050. One or more reference values may be periodically measured, entered into the user interface and sent to the reference memory 1050. If communication cannot be established between the wireless sensor electronics 120 and the user interface 210 when a new reference value is required, the sensor 100 will need calibration when it is re-connected. Alternatively, reference measurements are sent directly to the wireless sensor electronics 120. Some examples include: a BG meter with an IR transmitter sends a reference measurement to the wirelesses sensor electronics which include an IR receiver; a BG meter with RF communication capability sends a BG value to a wireless sensor electronics with an RF receiver; and a laboratory analyte measurement machine analyzes a blood sample and the result of the analysis is sent to an RF transmitter which transmits the result to the wireless sensor electronics.

Alternatively to the types of memory discussed above, a removable nonvolatile reference memory may be filled at the factory with reference values for calibrating one or more sensors. The removable nonvolatile reference memory may be a flash media such as a flash card, memory stick, and the like. The reference memory may be placed into the user interface and/or into the sensor electronics. The removable nonvolatile reference memory may be placed into a device such as, an auxiliary device, a meter, a BG meter, a palm pilot, a phone, a PDA, a handheld device, a patient monitor, a module that connects to a device, and the like. If a new sensor cannot be calibrated with a removable nonvolatile reference memory that is presently in a device, then the sensor will be accompanied with a new removable nonvolatile reference memory for use in a device.

An auxiliary device may provide power to a user interface, which in turn powers the sensor. The user interface may have a rechargeable power source that provides power to the user interface whenever power is not supplied by the auxiliary device. For example, an auxiliary device such as a patient monitor may provide power along a wire through a connector to a user interface; the user interface has a power supply; a sensor is connected by a wire to the user interface; the power from the auxiliary device powers a voltage regulator in the user interface, which powers the sensor. If the user interface is disconnected from the auxiliary device, the user interface power supply continues to supply power to the sensor. Alternatively, the auxiliary device may charge the user interface power supply whenever the auxiliary device is connected to the user interface, and the user interface may power the sensor whether or not the auxiliary device is connected to the user interface.

The sensor may be powered by sensor electronics, which are powered by a device such as an auxiliary device or a user interface. The sensor electronics may have a rechargeable power supply that keeps the sensor powered whenever power is not supplied by a device.

The power needed to operate a sensor may be generated at a device such as a user interface or an auxiliary device, carried over one or more wires, passed through a transformer and supplied to the sensor. Alternatively, the power may be passed through a regulator such as a voltage regulator and a current regulator before it is supplied to a sensor. The transformer may be located in the device or the transformer may be part of the wire or cable connecting the sensor to the device. The transformer also may be in the sensor electronics. The transformer keeps the sensor powered as long as the sensor is connected to the device. The transformer helps to remove a ground connection between the device and the sensor, and therefore isolates the patient from the ground voltage in the device.

The sensor signal may be passed to one or more devices before it is processed. For example, the sensor signal could be carried along a wire to a user interface, and then carried along a wire to an auxiliary device before it is processed. In another example, the sensor signal is carried to a computer, sent through a server or a router to a second computer, and then processed.

The user interface may process the sensor measurements to generate insulin delivery commands. The insulin delivery commands may be infusion rates. Alternatively, the insulin delivery commands may be insulin amounts.

An auxiliary device may process the sensor measurements to generate insulin delivery commands. Alternatively, sensor electronics may process the sensor measurements to generate insulin delivery commands.

The insulin delivery commands may be generated in the device that contains the measurement processor. Alternatively, the insulin delivery commands may be generated by a device that receives sensor measurements, such as an auxiliary device, a pump, and the like. Still alternatively, the insulin delivery commands are generated by an insulin infusion pump such as shown in U.S. Pat. Nos. 4,562,751, 4,678,408, 4,685,903, 5,080,653, 5,097,122, and 6,554,798, which are herein incorporated by reference.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A system for sensing blood glucose concentration of a person, the system comprising:

a sensor to sense blood glucose data;

sensor electronics attached to the sensor and adapted to communicate with the sensor, the sensor electronics including a sensor power supply to supply power to the sensor, said sensor power supply being activated when the sensor is connected to a device selected from the group consisting of a user interface and a patient monitor, said device being separate from said sensor electronics;

a user interface configured to communicate wirelessly with the sensor electronics; and a patient monitor configured to communicate wirelessly with the user interface and including a display to display information representative of the blood glucose data sensed by the sensor, wherein the sensor power supply comprises at least one rechargeable battery, and at least one of the user interface and the patient monitor includes a power source for providing power to the sensor electronics for recharging the at least one rechargeable battery; and wherein the sensor power supply continues to supply power to the sensor when the sensor electronics are not in communication with the user interface and the patient monitor.

2. The system of claim 1, wherein the sensor electronics further include memory to store information representative of the blood glucose data sensed by the sensor and to store reference values for calibration of the blood glucose data received from the sensor.

3. The system of claim 2, wherein the user interface includes an input for inputting information into the memory of the sensor electronics.

4. The system of claim 1, wherein the sensor electronics include a processor to process the blood glucose data received from the sensor.

5. A system for sensing blood glucose concentration of a person, the system comprising:

a sensor to sense blood glucose data;

sensor electronics attached to the sensor and adapted to communicate with the sensor, wherein the sensor includes a connector and the sensor electronics are attached to the sensor using the connector, and wherein the sensor electronics include a processor to process the blood glucose data received from the sensor and a sensor power supply to supply power to the sensor, said sensor power supply being activated when the sensor is connected to a device selected from the group consisting of a user interface and a patient monitor, said device being separate from said sensor electronics;

a user interface configured to communicate wirelessly with the sensor electronics; and a patient monitor configured to communicate wirelessly with the user interface and including a display to display information representative of the blood glucose data sensed by the sensor, wherein the sensor power supply comprises at least one rechargeable battery, and at least one of the user interface and the patient monitor includes a power source for providing power to the sensor electronics for recharging the at least one rechargeable battery; and wherein the sensor power supply continues to supply power to the sensor when the sensor electronics are not in communication with the user interface and the patient monitor.

6. A system for sensing blood glucose concentration of a person, the system comprising:

a real-time sensor to sense blood glucose data in real-time;

sensor electronics attached to the sensor and adapted to communicate with the sensor;

a user interface configured to communicate wirelessly with the sensor electronics; and a patient monitor configured to communicate wirelessly with the user interface and including a display to display information representative of the blood glucose data sensed by the sensor, wherein the sensor electronics are configured to communicate with a second user interface and include: (a) a sensor power supply comprising at least one rechargeable battery to supply power to the sensor, said power supply being activated when the sensor is connected to the user interface or the patient monitor, said user interface and patient monitor being separate from said sensor electronics, and at least one of the user interface and the patient monitor including a power source for providing power to the sensor electronics for recharging the at least one rechargeable battery, wherein the sensor power supply continues to supply power to the sensor when the sensor electronics are not in communication with the user interface and the patient monitor; and (b) memory to store information representative of the blood glucose data sensed by the sensor and to store reference values for calibration of the blood glucose data received from the sensor.

* * * * *